(12) United States Patent
Zambach et al.

(10) Patent No.: US 7,192,965 B2
(45) Date of Patent: Mar. 20, 2007

(54) 4-(3,3-DIHALO-ALLYLOXY)PHENOXY ALKYL DERIVATIVES

(75) Inventors: Werner Zambach, Basel (CH); Peter Renold, Basel (CH); Arthur Steiger, Basel (CH); Stephan Trah, Basel (CH); Roger Graham Hall, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 213 days.

(21) Appl. No.: 10/518,888

(22) PCT Filed: Jun. 27, 2003

(86) PCT No.: PCT/EP03/06846

§ 371 (c)(1),
(2), (4) Date: Dec. 21, 2004

(87) PCT Pub. No.: WO2004/002943

PCT Pub. Date: Jan. 8, 2004

(65) Prior Publication Data

US 2005/0245583 A1    Nov. 3, 2005

(30) Foreign Application Priority Data

Jun. 28, 2002    (CH) .................................. 1123/02

(51) Int. Cl.
*A01N 33/02*    (2006.01)
*C07C 333/00*    (2006.01)
*C07C 69/76*    (2006.01)
*C07C 327/00*    (2006.01)
*C07C 325/00*    (2006.01)
*C07C 49/23*    (2006.01)
*C07D 319/02*    (2006.01)

(52) U.S. Cl. ...................... 514/279; 514/277; 514/452; 514/464; 514/465; 514/466; 514/476; 514/482; 514/485; 514/486; 514/488; 514/489; 558/234; 558/236; 558/238; 558/239; 424/405

(58) Field of Classification Search ................ 514/279, 514/277, 452, 464, 465, 466, 476, 482, 485, 514/486, 488, 489; 558/234, 236, 238, 239; 544/88, 98; 546/106; 560/53, 54, 102; 564/23, 564/27, 28; 568/20, 39, 41; 424/405

See application file for complete search history.

(56) References Cited

U.S. PATENT DOCUMENTS 5,869,506 A    2/1999    Izumi et al.
5,922,880 A    7/1999    Sakamoto et al.
5,952,386 A *  9/1999    Matsuo et al. ............... 514/651

FOREIGN PATENT DOCUMENTS

WO    WO 9604228    2/1996
WO    96/15093      5/1996
WO    WO 9633160   10/1996
WO    WO 9727173    7/1997

*Primary Examiner*—Joseph K. McKane
*Assistant Examiner*—Michael P. Barker
(74) *Attorney, Agent, or Firm*—Jacqueline Haley

(57) ABSTRACT

Compounds of formula

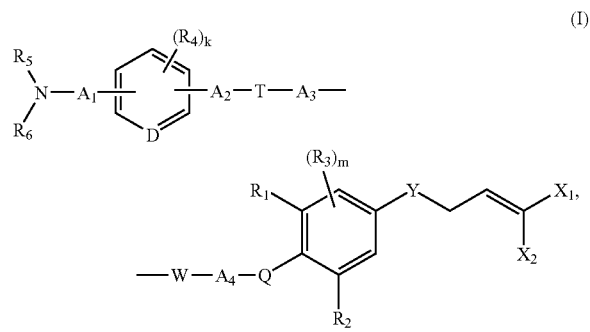

(I)

wherein
$A_1$, $A_2$ and $A_3$ are each independently of the others a bond or a $C_1$–$C_6$alkylene bridge;
$A_4$ is a $C_1$–$C_6$alkylene bridge;
D is CH or N;
W is, for example, O, $NR_7$ or S;
T is, for example, a bond, O, NH or $NR_7$;
Q is O, $NR_7$, S, SO or $SO_2$;
Y is O, $NR_7$, S, SO or $SO_2$;
$X_1$ and $X_2$ are each independently of the other fluorine, chlorine or bromine;
$R_1$, $R_2$ and $R_3$ are, for example, H, halogen, CN, nitro, $C_1$–$C_6$alkyl, $C_1$–$C_6$haloalkyl, $C_1$–$C_6$alkylcarbonyl or $C_2$–$C_6$alkenyl;
$R_4$ is, for example, H, halogen, CN, nitro or $C_1$–$C_6$alkyl;
$R_5$ and $R_6$ are, for example, H, CN, OH, $C_1$–$C_6$alkyl, $C_3$–$C_8$cycloalkyl, $C_3$–$C_8$cycloalkyl-$C_1$–$C_6$alkyl, $C_1$–$C_6$haloalkyl, $C_1$–$C_6$alkoxy or $C_1$–$C_6$haloalkoxy;
$R_7$ is H, $C_1$–$C_6$alkyl, $C_1$–$C_6$alkoxyalkyl or $C_1$–$C_6$alkylcarbonyl;
k, when D is nitrogen, is 1, 2 or 3; or, when D is CH, is 1, 2, 3 or 4; and
m is 1 or 2;
and, where applicable, their possible E/Z isomers, E/Z isomeric mixtures and/or tautomers, in each case in free form or in salt form,
a process for the preparation of those compounds and their use, pesticidal compositions in which the active ingredient has been selected from those compounds or an agrochemically acceptable salt thereof, a process for the preparation of those compositions and their use, plant propagation material treated with those compositions, and a method of controlling pests.

10 Claims, No Drawings

U.S. PATENT DOCUMENTS 6,071,861 A    6/2000   Sakamoto et al.
6,140,274 A    10/2000  Ikegami et al.
6,268,313 B1   7/2001   Sakamoto et al.
6,376,428 B1   4/2002   Sakamoto et al.
6,437,184 B1   8/2002   Ikegami et al.
6,448,444 B2   9/2002   Ikegami et al.
6,589,914 B2   7/2003   Sakamoto et al.

* cited by examiner

4-(3,3-DIHALO-ALLYLOXY)PHENOXY ALKYL DERIVATIVES

This application is a 371 of International Application No. PCT/EP03/06846 filed Jun. 27, 2003, which claims priority to CH 1123/02 filed Jun. 28, 2002, the contents of which are incorporated herein by reference.

The present invention relates (1) to compounds of formula

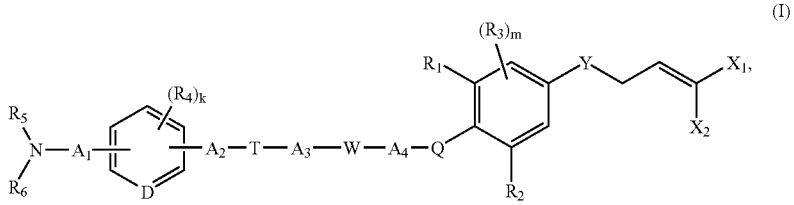

(I)

wherein $A_1$, $A_2$ and $A_3$ are each independently of the others a bond or a $C_1$–$C_6$alkylene bridge which is unsubstituted or substituted by from one to six identical or different substituents selected from $C_3$–$C_8$cycloalkyl, $C_3$–$C_8$cycloalkyl-$C_1$–$C_6$alkyl and $C_1$–$C_3$haloalkyl;

$A_4$ is a $C_1$–$C_6$alkylene bridge which is unsubstituted or substituted by from one to six identical or different substituents selected from $C_3$–$C_8$cycloalkyl, $C_3$–$C_8$cycloalkyl-$C_1$–$C_6$alkyl and $C_1$–$C_3$haloalkyl;

D is CH or N;

W is O, $NR_7$, S, SO, $SO_2$, —C(=O)—O—, —O—C(=O)—, —C(=O)—$NR_8$— or —$NR_8$—C(=O)—;

T is a bond, O, NH, $NR_7$, S, SO, $SO_2$, —C(=O)—O—, —O—C(=O)—, —C(=O)—$NR_8$— or —$NR_8$—C(=O)—;

Q is O, $NR_7$, S, SO or $SO_2$;

Y is O, $NR_7$, S, SO or $SO_2$;

$X_1$ and $X_2$ are each independently of the other fluorine, chlorine or bromine;

$R_1$, $R_2$ and $R_3$ are each independently of the others H, halogen, CN, nitro, $C_1$–$C_6$alkyl, $C_1$–$C_6$haloalkyl, $C_1$–$C_6$alkylcarbonyl, $C_2$–$C_6$alkenyl, $C_2$–$C_6$haloalkenyl, $C_2$–$C_6$alkynyl, $C_1$–$C_6$alkoxy, $C_1$–$C_6$haloalkoxy, $C_2$–$C_6$alkenyloxy, $C_2$–$C_6$haloalkenyloxy, $C_2$–$C_6$alkynyloxy, $C_1$–$C_6$alkoxycarbonyl or $C_2$–$C_6$haloalkenyloxy; the substituents $R_3$ being independent of one another when m is 2;

$R_4$ is H, halogen, CN, nitro, $C_1$–$C_6$alkyl, $C_1$–$C_6$haloalkyl, $C_1$–$C_6$alkylcarbonyl, $C_2$–$C_6$alkenyl, $C_2$–$C_6$haloalkenyl, $C_2$–$C_6$alkynyl, $C_1$–$C_6$alkoxy, $C_1$–$C_6$haloalkoxy, $C_2$–$C_6$alkenyloxy, $C_2$–$C_6$haloalkenyloxy, $C_2$–$C_6$alkynyloxy, $C_1$–$C_6$alkoxycarbonyl or $C_2$–$C_6$haloalkenyloxy; the substituents $R_4$ being independent of one another when k is greater than 1;

$R_5$ is H, CN, OH, $C_1$–$C_6$alkyl, $C_3$–$C_8$cycloalkyl, $C_3$–$C_8$cycloalkyl-$C_1$–$C_6$alkyl, $C_1$–$C_6$haloalkyl, $C_1$–$C_6$alkoxy, $C_1$–$C_6$haloalkoxy, $C_2$–$C_6$alkenyloxy, $C_2$–$C_6$haloalkenyloxy, $C_2$–$C_6$alkynyloxy, —C(=O)$R_9$, —C(=S)$R_9$, phenyl, benzyl; or phenyl, phenylcarbonyl or benzyl each of which is substituted in the aromatic ring by from one to five identical or different substituents selected from the group consisting of halogen, $C_1$–$C_6$alkyl, halo-$C_1$–$C_6$alkyl, $C_1$–$C_6$alkoxy, halo-$C_1$–$C_6$alkoxy, hydroxy, cyano and nitro;

$R_6$ is H, CN, $C_1$–$C_6$alkyl, $C_3$–$C_8$cycloalkyl, $C_3$–$C_8$cycloalkyl-$C_1$–$C_6$alkyl, $C_1$–$C_6$haloalkyl, —C(=O)$R_9$, —C(=S)$R_9$, phenyl, benzyl; or phenyl, phenylcarbonyl or benzyl each of which is substituted in the aromatic ring by from one to five identical or different substituents selected from the group consisting of halogen, $C_1$–$C_6$alkyl, halo-$C_1$–$C_6$alkyl, $C_1$–$C_6$alkoxy, halo-$C_1$–$C_6$alkoxy, hydroxy, cyano and nitro; or $R_5$ and $R_6$ together form a four- to eight-membered, straight-chain or branched alkylene bridge wherein a $CH_2$ group may have been replaced by O, S or $NR_{10}$, and the alkylene bridge is unsubstituted or substituted by from one to four identical or different substituents selected from $C_3$–$C_8$cycloalkyl, $C_3$–$C_8$cycloalkyl-$C_1$–$C_6$alkyl and $C_1$–$C_3$haloalkyl; or $R_6$ is —C(=O)$R_9$ or —C(=S)$R_9$, and $R_5$ and $R_9$ together form a three- to eight-membered, straight-chain or branched alkylene bridge wherein a $CH_2$ group may have been replaced by O, S or $NR_{10}$, and the alkylene bridge is unsubstituted or substituted by from one to four identical or different substituents selected from $C_3$–$C_8$cycloalkyl, $C_3$–$C_8$cycloalkyl-$C_1$–$C_6$alkyl and $C_1$–$C_3$haloalkyl; or $R_5$ and $R_6$ are each independently of the other —C(=O)$R_9$ or —C(=S)$R_9$, and the two $R_9$ together form a two- to eight-membered, straight-chain or branched alkylene bridge wherein a $CH_2$ group may have been replaced by O, S or $NR_{10}$; and the alkylene bridge is unsubstituted or substituted by from one to four identical or different substituents selected from $C_3$–$C_8$cycloalkyl, $C_3$–$C_8$cycloalkyl-$C_1$–$C_6$alkyl and $C_1$–$C_3$haloalkyl;

$R_7$ is H, $C_1$–$C_6$alkyl, $C_1$–$C_3$haloalkyl, $C_1$–$C_3$haloalkylcarbonyl, $C_1$–$C_6$alkoxyalkyl $C_1$–$C_6$alkylcarbonyl or $C_3$–$C_8$cycloalkyl;

$R_8$ is H, $C_1$–$C_6$alkyl, $C_1$–$C_3$haloalkyl, $C_1$–$C_3$haloalkylcarbonyl, $C_1$–$C_6$alkoxyalkyl $C_1$–$C_6$alkylcarbonyl or $C_3$–$C_8$cycloalkyl;

$R_9$ is $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_1$–$C_6$alkoxy, $C_1$–$C_6$haloalkoxy, $C_2$–$C_6$alkenyloxy, $C_2$–$C_6$haloalkenyloxy, $C_2$–$C_6$alkynyloxy, $C_3$–$C_6$cycloalkyl, phenyl, benzyl; or phenyl or benzyl each of which is unsubstituted or substituted by from one to three identical or different substituents selected from halogen, CN, nitro, $C_1$–$C_6$alkyl, $C_1$–$C_6$haloalkyl, $C_1$–$C_6$alkylcarbonyl, $C_2$–$C_6$alkenyl, $C_2$–$C_6$haloalkenyl, $C_2$–$C_6$alkynyl, $C_1$–$C_6$alkoxy, $C_1$–$C_6$haloalkoxy, $C_1$–$C_6$alkoxycarbonyl, $C_1$–$C_3$haloalkoxycarbonyl and $C_2$–$C_6$haloalkenyloxy;

$R_{10}$ is H, $C_1$–$C_6$alkyl, $C_1$–$C_3$haloalkyl, $C_1$–$C_3$haloalkylcarbonyl, $C_1$–$C_6$alkoxyalkyl, $C_1$–$C_6$alkylcarbonyl or $C_3$–$C_8$cycloalkyl;

k, when D is nitrogen, is 1, 2 or 3; or, when D is CH, is 1, 2, 3 or 4; and m is 1 or 2;

and, where applicable, their possible E/Z isomers, E/Z isomeric mixtures and/or tautomers, in each case in free form or in salt form, to a process for the preparation of those compounds, E/Z isomers and tautomers and to their use, to pesticidal compositions in which the active ingredient has been selected from those compounds, E/Z isomers and tautomers, and to a process for the preparation of those compositions and to their use, to intermediates and, where applicable, their possible E/Z isomers, E/Z isomeric mixtures and/or tautomers, in free form or in salt form, for the preparation of those compounds, where applicable to tautomers, in free form or in salt form, of those intermediates and to a process for the preparation of those intermediates and their tautomers and to their use.

Certain dihalovinyl derivatives are proposed in the literature as active ingredients in pesticidal compositions. The biological properties of those known compounds are not entirely satisfactory in the field of pest control, however, for which reason there is a need to provide further compounds having pesticidal properties, especially for controlling insects and members of the order Acarina, that problem being solved according to the invention by the provision of the present compounds of formula (I).

The compounds of formula (I) and, where applicable, their tautomers are able to form salts, e.g. acid addition salts. The latter are formed, for example, with strong inorganic acids, such as mineral acids, e.g. sulfuric acid, a phosphoric acid or a hydrohalic acid, with strong organic carboxylic acids, such as unsubstituted or substituted, e.g. halo-substituted, $C_1$–$C_4$alkanecarboxylic acids, for example acetic acid, saturated or unsaturated dicarboxylic acids, e.g. oxalic, malonic, maleic, fumaric or phthalic acid, hydroxycarboxylic acids, e.g. ascorbic, lactic, malic, tartaric or citric acid, or benzoic acid, or with organic sulfonic acids, such as unsubstituted or substituted, e.g. halo-substituted, $C_1$–$C_4$alkane- or aryl-sulfonic acids, e.g. methane- or p-toluene-sulfonic acid. Furthermore, compounds of formula (I) having at least one acid group are able to form salts with bases. Suitable salts with bases are, for example, metal salts, such as alkali metal or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethyl-propyl-amine, or a mono-, di- or tri-hydroxy-lower alkylamine, e.g. mono-, di- or tri-ethanolamine. It may also be possible for corresponding internal salts to be formed. On the one hand the free form is preferred. Of the salts of compounds of formula (I), preference is given to agrochemically advantageous salts. Hereinabove and hereinbelow any reference to the free compounds of formula (I) or to their salts is to be understood as including, where appropriate, the corresponding salts or the free compounds of formula (I), respectively. The same applies to tautomers of compounds of formula (I) and their salts.

The general terms used hereinabove and hereinbelow have the meanings given below, unless defined otherwise.

Halogen, as a group per se and as a structural element of other groups and compounds, such as haloalkyl, halocycloalkyl, haloalkenyl, haloalkynyl and haloalkoxy, is fluorine, chlorine, bromine or iodine, especially fluorine, chlorine or bromine, more especially fluorine or chlorine, especially chlorine.

Unless defined otherwise, carbon-containing groups and compounds each contain from 1 up to and including 20, preferably from 1 up to and including 18, especially from 1 up to and including 10, more especially from 1 up to and including 6, especially from 1 up to and including 4, especially from 1 up to and including 3, more especially 1 or 2, carbon atoms; methyl is especially preferred.

Alkylene is a straight-chain or branched bridging member and is especially —$CH_2$—, —$CH_2CH_2$—, —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH(CH_3)$—, —$CH_2(CH_3)CH_2$—$CH_2$—, —$CH(C_2H_5)$—, —$C(CH_3)_2$—, —$CH(CH_3)CH_2$—, —$CH(CH_3)CH(CH_3)$—, or —$CH_2C(CH_3)_2$—$CH_2$—.

Alkyl, as a group per se and as a structural element of other groups and compounds, such as haloalkyl, alkoxy, alkoxyalkyl, haloalkoxy, alkoxycarbonyl, alkylthio, haloalkylthio, alkylsulfonyl and alkylsulfonyloxy, is—in each case giving due consideration to the number of carbon atoms contained in the group or compound in question—either straight-chained, e.g. methyl, ethyl, n-propyl, n-butyl, n-hexyl, n-octyl, n-decyl, n-dodecyl, n-hexadecyl or n-octadecyl, or branched, e.g. isopropyl, isobutyl, sec-butyl, tert-butyl, isopentyl, neopentyl or isohexyl.

Alkenyl and alkynyl—as groups per se and as structural elements of other groups and compounds, such as haloalkenyl, haloalkynyl, alkenyloxy, haloalkenyloxy, alkynyloxy or haloalkynyloxy—are straight-chain or branched and each contains two or preferably one unsaturated carbon-carbon bond(s). There may be mentioned by way of example vinyl, prop-2-en-1-yl, 2-methylprop-2-en-1-yl, but-2-en-1-yl, but-3-en-1-yl, prop-2-yn-1-yl, but-2-yn-1-yl and but-3-yn-1-yl.

Cycloalkyl—as a group per se and as a structural element of other groups and compounds, such as alkyl—is cyclopropyl, cyclobutyl, cyclopentyl, cyclohexyl, cycloheptyl or cyclooctyl. Cyclopentyl and cyclohexyl, and especially cyclopropyl, are preferred.

Halo-substituted carbon-containing groups and compounds, such as haloalkyl and haloalkoxy, may be partially halogenated or perhalogenated, the halogen substituents in the case of polyhalogenation being the same or different. Examples of haloalkyl—as a group per se and as a structural element of other groups and compounds, such as haloalkoxy—are methyl substituted from one to three times by fluorine, chlorine and/or bromine, such as $CHF_2$, $CF_3$ or $CH_2Cl$; ethyl substituted from one to five times by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CH_2CH_2Cl$, $CF_2CHBr_2$, $CF_2CHClF$, $CF_2CHBrF$ or $CClFCHClF$; propyl or isopropyl substituted from one to seven times by fluorine, chlorine and/or bromine, such as $CH_2CHBrCH_2Br$, $CF_2CHFCF_3$, $CH_2CF_2CF_3$, $CF_2CF_2CF_3$, $CH(CF_3)_2$ or $CH_2CH_2CH_2Cl$; and butyl or an isomer thereof substituted from one to nine times by fluorine, chorine and/or bromine, such as $CF(CF_3)CHFCF_3$, $CF_2(CF_2)_2CF_3$ or $CH_2(CF_2)_2CF_3$.

Aryl is especially phenyl or naphthyl, preferably phenyl.

Preferred embodiments within the scope of the invention are (2) compounds according to (1) of formula (I) wherein $X_1$ and $X_2$ are chlorine or bromine, especially chlorine;

(3) compounds according to (1) or (2) of formula (I) wherein $A_1$ is a bond;

(4) compounds according to (1) to (3) of formula (I) wherein the group $A_2$-T-$A_3$ is a bond;

(5) compounds according to (1) to (4) of formula (I) wherein W is oxygen, —C(=O)O— or —C(=O)NH—, especially O;

(6) compounds according to (1) to (5) of formula (I) wherein $A_4$ is a straight-chain alkylene bridge, especially ethylene, propylene or butylene, more especially propylene;

(7) compounds according to (1) to (6) of formula (I) wherein Q is oxygen;

(8) compounds according to (1) to (7) of formula (I) wherein Y is oxygen;

(9) compounds according to (1) to (8) of formula (I) wherein $R_1$ and $R_2$ are bromine or chlorine, especially chlorine;

(10) compounds according to (1) to (9) of formula (I) wherein $R_3$ is hydrogen;

(11) compounds according to (1) to (10) of formula (I) wherein $R_4$ is hydrogen;

(12) compounds according to (1) to (11) of formula (I) wherein $R_5$ is H, $C_1$–$C_6$alkyl, $C_3$–$C_8$cycloalkyl, $C_3$–$C_8$cycloalkyl-$C_1$–$C_6$alkyl, $C_1$–$C_6$haloalkyl, $C_1$–$C_6$alkoxy, $C_1$–$C_6$haloalkoxy, $C_2$–$C_6$alkenyloxy, $C_2$–$C_6$haloalkenyloxy, $C_2$–$C_6$alkynyloxy;

(13) compounds according to (1) to (12) of formula (I) wherein $R_6$ is —C(=O)$R_9$ or —C(=S)$R_9$, and $R_9$ is $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_1$–$C_6$alkoxy, $C_1$–$C_6$haloalkoxy, $C_2$–$C_6$alkenyloxy, $C_2$–$C_6$haloalkenyloxy, $C_2$–$C_6$alkynyloxy, $C_3$–$C_6$cycloalkyl or phenyl;

(14) compounds according to (1) to (3) and (5) to (12) of formula (I) wherein $A_2$ is a bond, T is oxygen and $A_3$ is a $C_1$–$C_6$alkylene bridge;

(15) compounds according to (1) to (3) of formula (I) wherein $A_2$ is a bond, T is —C(=O)O— wherein the oxygen is bonded to $A_3$, or is —C(=O)NH— wherein NH is bonded to $A_3$, and $A_3$ is a $C_1$–$C_6$alkylene bridge.

Special preference is given to the compounds listed in the Tables.

The invention relates also to a process for the preparation of a compound of formula (I), or a salt thereof, wherein (a) a compound of formula $$\left[ R_5\underset{R_6}{\overset{}{N}}-A_1\underset{D}{\overset{(R_4)_k}{\diagdown}}A_2-T-A_3-W-A_4-Q\underset{R_2}{\overset{R_1}{\diagdown}}\overset{(R_3)_m}{\diagdown}Z_1 \right]_G \quad (II)$$

wherein $A_1$, $A_2$, $A_3$, $A_4$, D, W, Q, T, $R_1$, $R_2$, $R_3$, $R_4$, $R_5$, $R_6$, m and k are as defined for formula (I) under (1), $Z_1$ is —C(=O)$R_{11}$ and $R_{11}$ is H or $C_1$–$C_6$alkyl, is converted in the presence of an oxidising agent, especially a peracid, into a compound of formula $$G\text{-}Z_{2a} \quad (IIIa);$$

wherein $Z_{2a}$ is O—C(=O)—$R_{12}$ and $R_{12}$ is $C_1$–$C_6$alkyl, and G denotes the part of the formula in the brackets designated G in formula (II); either ($b_1$) a compound of formula (IIIa) above or of formula $$G\text{-}Z_{2b} \quad (IIIb),$$

wherein G denotes the part of the formula in the brackets designated G in formula (II), $Z_{3b}$ is a radical of formula —Y—C(=O)$R_{13}$, W is as defined for formula (I) under (1), and $R_{13}$ is $C_1$–$C_{12}$alkyl unsubstituted or substituted by from one to three identical or different halogen substituents, or is phenyl unsubstituted or substituted by from one to three identical or different substituents selected from halogen, CN, nitro, $C_1$–$C_6$alkyl, $C_1$–$C_6$haloalkyl, $C_1$–$C_6$alkylcarbonyl, $C_2$–$C_6$alkenyl, $C_2$–$C_6$haloalkenyl, $C_2$–$C_6$alkynyl, $C_1$–$C_6$alkoxy, $C_1$–$C_6$haloalkoxy, $C_1$–$C_6$alkoxycarbonyl and $C_2$–$C_6$haloalkenyloxy, is converted by hydrolytic cleavage into a compound of formula $$G\text{-}Z_3 \quad (IV),$$

wherein G denotes the part of the formula in the brackets designated G in formula (II), $Z_3$ is YH, and Y is as defined for formula (I) under (1); or (c) a compound of formula $$G\text{-}Z_4 \quad (V),$$

wherein $Z_4$ is Y—$CH_2$-phenyl, wherein the phenyl radical is unsubstituted or substituted by from one to three identical or different substituents selected from halogen, CN, nitro, $C_1$–$C_6$alkyl, $C_1$–$C_6$haloalkyl, $C_1$–$C_6$alkylcarbonyl, $C_2$–$C_6$alkenyl, $C_2$–$C_6$haloalkenyl, $C_2$–$C_6$alkynyl, $C_1$–$C_6$alkoxy, $C_1$–$C_6$haloalkoxy, $C_1$–$C_6$alkoxycarbonyl or $C_2$–$C_6$haloalkenyloxy, G denotes the part of the formula in the brackets designated G in formula (II), and Y is as defined for formula (I), is converted by removal of the benzyl group into a compound of formula (IV), as defined above;

(d) the compound of formula (IV) so obtained is reacted in the presence of a base with a compound of formula $$\text{Hal}\diagdown\overset{O-\text{alkyl}}{\underset{O-\text{alkyl}}{\diagup}}$$

wherein Hal is halogen, preferably bromine or chlorine, and alkyl is $C_1$–$C_6$alkyl, or the two alkyl radicals together form a $C_3$–$C_8$alkylene bridge, to form a compound of formula $$G\text{-}Z_5 \quad (VI),$$

wherein G denotes the part of the formula in the brackets designated G in formula (II), and $Z_5$ is $$Y\diagdown\overset{O-\text{alkyl}}{\underset{O-\text{alkyl}}{\diagup}},$$

wherein alkyl and Y are as defined above;

(e) the compound of formula (VI) so obtained is converted by deprotection of the acetal function in the presence of an acid into a compound of formula $$G\text{-}Z_6 \quad (VII),$$

wherein $Z_6$ is a group —Y—$CH_2$—C(=O)H, G is as defined above for the compound of formula (II), and Y is as defined for formula (I) under (1), either ($f_1$) for the preparation of a compound of formula (I) wherein $X_1$ and $X_2$ are chlorine or bromine, a compound of formula (VII) is reacted in the presence of a phosphine with a compound of formula C(X)$_4$ wherein X is chlorine or bromine; or ($f_2$) for the preparation of a compound of formula (I) wherein $X_1$ and $X_2$ are chlorine, a compound of formula (VII) is reacted first with $CCl_3$—COOH or with chloroform in the presence of a strong base, then with acetic anhydride and subsequently with powdered zinc in acetic acid; or ($f_3$) for the preparation of a compound of formula (I) wherein $X_1$ is fluorine and $X_2$ is chlorine or bromine, a compound of formula (VII) is reacted first with a compound of the formula $CF_2X_2$, of the formula $CFX_3$, of the formula $CF_2XC(=O)ONa$ or of the formula $CFX_2C(=O)ONa$, in the presence of a phosphine; or ($g_1$) for the preparation of a compound of formula (I) wherein $X_1$ and $X_2$ are chlorine or bromine, a compound of formula (IV) is reacted in the presence of base with a compound of formula

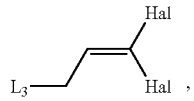

wherein $L_3$ is a leaving group, preferably chlorine or bromine, and Hal is chlorine or bromine; or ($g_2$) for the preparation of a compound of formula (I) wherein $X_1$ and $X_2$ are chlorine or bromine, a compound of formula (IVa) or (IVb) is reacted in the presence of a base with a compound of formula

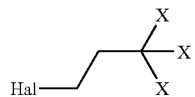

wherein Hal is halogen and X is chlorine or bromine.

The invention relates also to (h) a process for the preparation of a compound of formula (I), as defined under (1), and wherein Q is O, $NR_7$ or S, and $R_7$ is as defined for formula (I) under (1), wherein a compound of formula

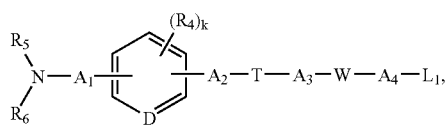

(VIII)

wherein $A_1$, $A_2$, $A_3$, $A_4$, D, W, T, $R_4$, $R_5$, $R_6$ and k are as defined for formula (I) under (1) and $L_1$ is a leaving group, in the presence of a base with a compound of formula

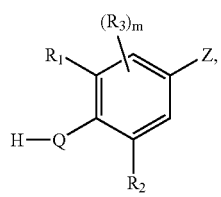

(IX)

wherein $R_1$, $R_2$, $R_3$ and m are as defined for formula (I) under (1), Q is O, $NR_7$ or S and Z is one of the radicals $Z_1$ to $Z_6$ as defined for the above formulae (II) to (VII), and $R_7$ is as defined for formula (I) under (1), and the resulting compound of formula

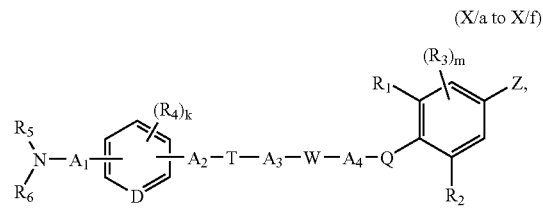

(X/a to X/f)

wherein $A_1$, $A_2$, $A_3$, $A_4$, D, W, Q, T, $R_1$, $R_2$, $R_3$, $R_4$, $R_5$, $R_6$, m and k are as defined for formula (I) under (1) and Z is one of the radicals $Z_1$ to $Z_6$ as defined for formulae (II) to (VII) indicated above, is, as necessary, that is to say according to the meaning of the radical Z, reacted further analogously to one or more of process steps (a) to (g).

In the compounds of formulae X/a to X/f, Z in compound X/a has the same meanings as $Z_1$ in the compound of formula (II), and Z in compound X/b has the same meanings as $Z_2$ as defined for formula (III), and so on.

The invention relates also to ($i_1$) a process for the preparation of a compound of formula (I) as defined above wherein W is O, $NR_7$, S, —O—C(=O)— or —$NR_8$—C(=O)—, and $R_7$ and $R_8$ are as defined for formula (I) under (1), wherein a compound of formula

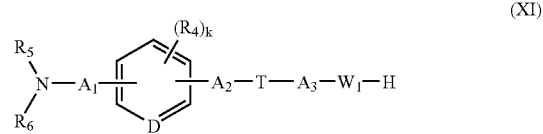

(XI)

wherein $A_1$, $A_2$, $A_3$, D, T, $R_4$, $R_5$, $R_6$ and k are as defined for formula (I) under (1), $W_1$ is O, $NR_7$, S or —$NR_8$— and $R_7$ is as defined for formula (I) under (1), is reacted with a compound of formula

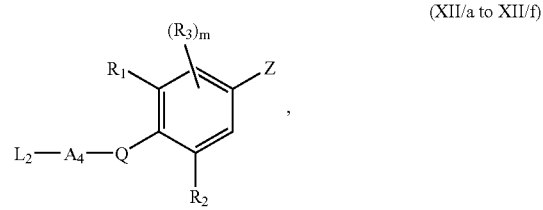

(XII/a to XII/f)

wherein $A_4$, $R_1$, $R_2$, $R_3$, Q and m are as defined for formula (I) under (1), $L_2$ is a leaving group or a group Hal-C(=O)— wherein Hal is a halogen atom, preferably chlorine or bromine, and Z is one of the radicals $Z_1$ to $Z_6$ as defined in formulae (II) to (VII) indicated above; or ($i_2$) for the preparation of a compound of formula (I) as defined above wherein W is O, $NR_7$, S, —C(=O)—O— or —C(=O)—NR$_8$—, and R$_7$ and R$_8$ are as defined for formula (I) under (1), wherein a compound of formula

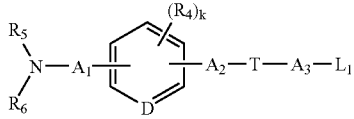
(XIII)

wherein A$_1$, A$_2$, A$_3$, D, T, R$_4$, R$_5$, R$_6$ and k are as defined for formula (I) under (1), and L$_1$ is a leaving group or a group —C(=O)-Hal wherein Hal is a halogen atom, preferably chlorine or bromine, is reacted with a compound of formula

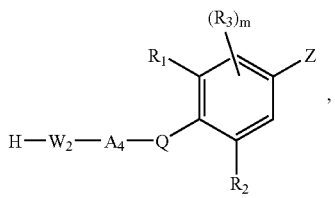
(XIV/a to XIV/f)

wherein W$_2$ is O, NR$_7$, S or NR$_8$, and R$_7$ and R$_8$ are as defined for formula (I) under (1), and a resulting compound of formula (Xa) to (Xf) as defined above is, as necessary, that is to say according to the meaning of the radical Z, reacted further analogously to one or more of process steps (a) to (g).

In the compounds of formulae XII/a to XII/f and XIV/a to XIV/f, the radicals Z are as defined above for the compounds X/a to X/f; that is to say, for example, Z in the compound of formula XII/a has the same meanings as Z$_1$ in the compound of formula (II), and Z in compound XII/b has the same meanings as Z$_2$ as defined for formula (III), and so on.

The invention relates also to (k) a process for the preparation of a compound of formula (I) as defined above under (1), wherein a compound of formula (VIII) as defined above is reacted in the presence of a base with a compound of formula

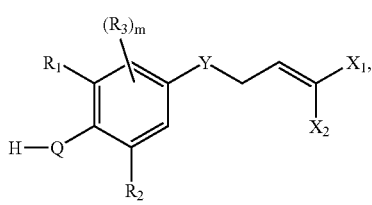
(XV)

wherein R$_1$, R$_2$, R$_3$, Q, X$_1$, X$_2$, Y and m are as defined for formula (I) under (1).

The invention relates also to (l) a process for the preparation of a compound of formula (I) as defined above under (1), wherein a compound of formula (XI) as defined above is reacted in a manner analogous to process variant (i) with a compound of formula

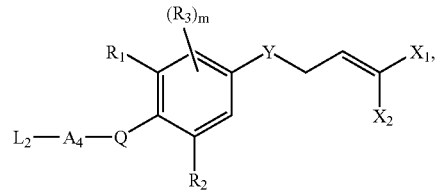
(XVI)

wherein A$_4$, R$_1$, R$_2$, R$_3$, Q, Y, X$_1$, X$_2$ and m are as defined for formula (I) under (1), and L$_2$ is as defined for formula (XII).

The compounds of formulae (IIIa) and (IIIb) wherein R$_1$ and R$_2$ are halogen can be obtained by reacting a compound of formula

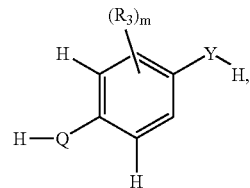
(XVII)

wherein R$_3$, Q, Y and m are as defined for formula (I) under (1) with a compound of the formula Hal-C(=O)—R$_{12}$ wherein R$_{12}$ is as defined above, halogenating the resulting compound of formula

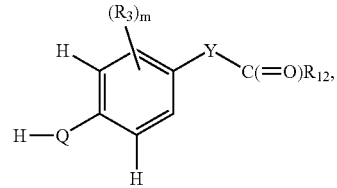
(XVIII)

wherein R$_3$, Q, Y and m are as defined for formula (I) under (1), and further reacting the resulting compound of formula

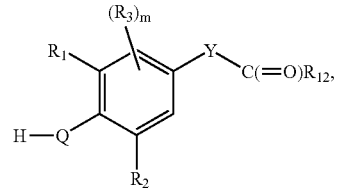
(XIX)

wherein R$_3$, Q, Y and m are as defined for formula (I) under (1) and R$_1$ and R$_2$ are halogen, analogously to Process (k).

The reactions described hereinabove and hereinbelow are carried out in a manner known per se, for example in the absence or, if necessary, in the presence of a suitable solvent or diluent or of a mixture thereof, the reactions being carried out, as required, with cooling, at room temperature or with heating, for example in a temperature range of approximately from −80° C. to the boiling temperature of the reaction mixture, preferably from approximately −20° C. to approximately +150° C., and, if necessary, in a closed vessel, under pressure, under an inert gas atmosphere and/or under anhydrous conditions. Especially advantageous reaction conditions can be found in the Examples.

A leaving group, for example the leaving groups $L_1$ and $L_2$ defined above, or a counter-ion is to be understood hereinbefore and hereinbelow as being any removable group that customarily comes into consideration for chemical reactions, such as are known to the person skilled in the art; especially OH, halogens, such as fluorine, chlorine, bromine, iodine, —O—Si($C_1$–$C_8$alkyl)$_3$, —O-aryl, —S—($C_1$–$C_8$alkyl), —S-aryl, —O—S(=O)$_2$U, —S(=O)U or —S(=O)$_2$U, wherein U is unsubstituted or substituted $C_1$–$C_8$alkyl, $C_2$–$C_8$alkenyl, $C_2$–$C_8$alkynyl, unsubstituted or substituted aryl or unsubstituted or substituted benzyl. Especially preferred as leaving group are chlorine or bromine, mesylate, triflate, tosylate, especially chlorine; or chloride or bromide, especially chloride.

Process (a): The reaction is carried out in acetic acid or a halogenated hydrocarbon, such as dichloromethane, at temperatures of from −20° C. to 100° C., preferably at from 20° C. to 50° C. As oxidising agents there are used, for example, hydrogen peroxide, a peracid, such as peracetic acid, trifluoroperacetic acid, 3-chloroperbenzoic acid or a mixture thereof, such as sodium perborate in acetic acid.

Process (b): The reaction is preferably carried out in an alcohol, such as methanol, ethanol or an alcohol/water mixture, in the presence of an inorganic base, such as NaOH or KOH, and at temperatures of from 0° C. to 150° C., preferably from 20° C. to 80° C. Alternatively aminolysis with a primary amine, such as n-butylamine, can be carried out in a hydrocarbon, such as toluene or benzene, at temperatures of from 0° C. to 150° C., preferably at from 20° C. to 80° C.

Process (c): Depending upon the nature of the benzyl substituent to be removed, the reaction can be carried out, for example, under a hydrogen atmosphere, at a pressure of from 1 to 150 bar, especially at from 1 to 20 bar, and with the addition of a catalyst, such as palladium/carbon, in an alcohol or ether. The preferred reaction temperature is from 0° C. to 120° C., especially from 20° C. to 80° C.

Processes (d) and (g): The reaction is preferably carried out in the presence of a base, such as potassium or sodium carbonate, in acetone or dimethylformamide, at temperatures of from 0° C. to 150° C., preferably from 20° C. to 80° C. If necessary, catalytic amounts of potassium iodide or sodium iodide, or phase transfer catalysts, such as crown ethers of quaternary ammonium salts, are added.

Process (e): The reaction is preferably carried out in acetone, dichloromethane, acetic acid, or especially in water, optionally with the addition of a mineral acid, at temperatures of from 0° C. to 120° C., preferably at from 20° C. to 50° C. For complete cleavage of the acetal it is preferable to add a strong mineral acid, for example hydrochloric acid, sulfuric acid or 4-toluenesulfonic acid.

Process (f): For the preparation of the difluoro-, dichloro-, dibromo-, chlorofluoro- and bromofluoro-vinyl compounds, reaction with $CCl_4$, $CBr_4$, $CF_2X_2$, $CFX_3$, $CF_2XC(=O)ONa$ or $CFX_2C(=O)ONa$ wherein X is bromine or chlorine is carried out in the presence of a trialkyl- or triaryl-phosphine, optionally with the addition of powdered zinc. The reaction is carried out in an inert solvent such as, for example, benzene or toluene, or an ether, such as diethyl ether, diisopropyl ether, dioxane or tetrahydrofuran, at temperatures of from 0° C. to 150° C., preferably at from 20° C. to 80° C.

For the preparation of the dichlorovinyl compounds it is also possible for the process to be carried out in dimethylformamide, benzene, toluene, or in an ether, at temperatures of from 0° C. to 120° C., preferably from 20° C. to 80° C., and in the presence of trichloroacetic acid/sodium trichloroacetate, then by addition of acetic anhydride, optionally with the addition of base, for example triethylamine, and finally by addition of zinc and acetic acid.

Processes (h) and (k): The reaction is preferably carried out in an ether, dimethylformamide, dimethylacetamide or N-methylpyrrolidone, at temperatures of from 0° C. to 150° C., preferably at from 20° C. to 80° C., with the addition of a base, such as potassium or sodium carbonate. Alternatively a coupling reagent, for example azodicarboxylic acid diethyl or diisopropyl ester and triphenylphosphine, can be used.

Processes (i) and (l):

Where $L_2$ is a group Hal-C(=O)—, the process can be carried out in an inert solvent, such as in an ether or in toluene, at from 0° C. to 80° C., and in the presence of a suitable base, for example a trialkylamine.

In the other cases the reaction is carried out in an ether, in an amide, such as dimethylformamide or N-methylpyrrolidone, and at from 0° C. to 150° C. Sodium hydride, for example, can be used as base.

Compounds of formula (I) obtainable in accordance with the process or by other means can be converted into other compounds of formula (I) in a manner known per se by replacement of one or more substituents in the starting compound of formula (I) in customary manner by another (other) substituent(s) according to the invention.

In the case of such replacement, depending upon the choice of reaction conditions and starting materials suitable therefor, it is possible for only one substituent to be replaced by another substituent according to the invention in a reaction step or for a plurality of substituents to be replaced by other substituents according to the invention in the same reaction step.

Salts of compounds of formula (I) can be prepared in a manner known per se. For example, salts of compounds of formula (I) with bases are obtained by treatment of the free compounds with a suitable base or with a suitable ion exchange reagent.

Salts of compounds of formula (I) can be converted into the free compounds of formula (I) in customary manner, for example by treatment with a suitable acid or with a suitable ion exchange reagent.

Salts of compounds of formula (I) can be converted in a manner known per se into other salts of a compound of formula (I).

The compounds of formula (I), in free form or in salt form, may be in the form of one of the possible isomers or in the form of a mixture thereof, for example, depending on the number of asymmetric carbon atoms occurring in the molecule and their absolute and relative configuration, and/or depending on the configuration of non-aromatic double bonds occurring in the molecule, in the form of pure isomers, such as antipodes and/or diastereoisomers, or in the form of mixtures of isomers, such as mixtures of enantiomers, for example racemates, mixtures of diastereoisomers or mixtures of racemates. The invention relates both to the pure isomers and to all possible mixtures of isomers and is to be interpreted as such hereinbefore and hereinafter, even if stereochemical details are not mentioned specifically in every case.

Mixtures of diastereoisomers, mixtures of racemates and mixtures of double bond isomers of compounds of formula (I), in free form or in salt form, which may be obtained by the process according to the invention—depending upon the starting materials and procedures chosen—or by some other method, can be separated into the pure diastereoisomers or racemates in known manner on the basis of the physico-chemical differences between the constituents, for example by means of fractional crystallisation, distillation and/or chromatography.

Mixtures of enantiomers, such as racemates, that are obtainable in a corresponding manner can be resolved into the enantiomers by known methods, for example by recrystallisation from an optically active solvent, by chromatography on chiral adsorbents, for example high pressure liquid chromatography (HPLC) on acetylcellulose, with the aid of suitable microorganisms, by cleavage with specific, immobilised enzymes, via the formation of inclusion compounds, for example using chiral crown ethers, only one enantiomer being complexed, or by conversion into diastereoisomeric salts and separation of the mixture of diastereoisomers so obtained, for example on the basis of their different solubilities by fractional crystallisation, into the diastereoisomers, from which the desired enantiomer can be freed by the action of suitable agents.

Apart from by separation of corresponding mixtures of isomers, pure diastereoisomers or enantiomers can be obtained according to the invention also by generally known methods of diastereoselective or enantioselective synthesis, for example by carrying out the process according to the invention using starting materials having correspondingly suitable stereo-chemistry.

In each case it is advantageous to isolate or synthesise the biologically more active isomer, e.g. enantiomer or diastereoisomer, or isomeric mixture, e.g. enantiomeric mixture or diastereoisomeric mixture, where the individual components have different biological activity.

The compounds of formula (I), in free form or salt form, can also be obtained in the form of their hydrates and/or may include other solvents, for example solvents which may have been used for the crystallisation of compounds in solid form.

The invention relates to all those embodiments of the process according to which a compound obtainable as starting material or intermediate at any stage of the process is used as starting material and some or all of the remaining steps are carried out or a starting material is used in the form of a derivative or salt and/or its racemates or antipodes or, especially, is formed under the reaction conditions.

In the process of the present invention it is preferable to use those starting materials and intermediates, in each case in free form or in salt form, which result in the compounds of formula (I) and their salts described at the beginning as being especially valuable.

The invention relates especially to the preparation processes described in Examples P1 to P4.

The invention relates also to the intermediates of formulae (II) to (XIX), where novel, and, where applicable, to their possible E/Z isomers, E/Z isomeric mixtures and/or tautomers, in each case in free form or in salt form. The preferences applying to such compounds are the same as those for the compounds of formula (I).

In the area of pest control, the compounds of formula (I) according to the invention are active ingredients exhibiting valuable preventive and/or curative activity with a very advantageous biocidal spectrum even at low rates of concentration, while being well tolerated by warm-blooded animals, fish and plants. The active ingredients according to the invention are effective against all or individual development stages of normally sensitive animal pests, but also of resistant animal pests, such as insects and members of the order Acarina. The insecticidal or acaricidal activity of the active ingredients according to the invention may manifest itself directly, i.e. in the mortality of the pests, which occurs immediately or only after some time, for example during moulting, or indirectly, for example in reduced ovi-position and/or hatching rate, good activity corresponding to a mortality of at least 50 to 60%.

The said animal pests include, for example, those mentioned in European Patent Application EP-A-736 252, page 5, line 55, to page 6, line 55. The pests mentioned therein are therefore included by reference in the subject matter of the present invention. The active ingredients according to the invention are especially suitable for controlling *Boophilus microplus, Nilaparvata lugens* and *Tetranychus urticae*, more especially for controlling those pests in crops of vegetables, fruit and rice.

The active ingredients according to the invention can be used to control, i.e. to inhibit or destroy, pests of the mentioned type occurring especially on plants, more especially on useful plants and ornamentals in agriculture, in horticulture and in forestry, or on parts of such plants, such as the fruits, blossoms, foliage, stems, tubers or roots, while in some cases parts of plants that grow later are still protected against those pests.

Target crops include especially cereals, such as wheat, barley, rye, oats, rice, maize and sorghum; beet, such as sugar beet and fodder beet; fruit, e.g. pomes, stone fruit and soft fruit, such as apples, pears, plums, peaches, almonds, cherries and berries, e.g. strawberries, raspberries and blackberries; leguminous plants, such as beans, lentils, peas and soybeans; oil plants, such as rape, mustard, poppy, olives, sunflowers, coconut, castor oil, cocoa and groundnuts; cucurbitaceae, such as marrows, cucumbers and melons; fibre plants, such as cotton, flax, hemp and jute; citrus fruits, such as oranges, lemons, grapefruit and mandarins; vegetables, such as spinach, lettuce, asparagus, cabbages, carrots, onions, tomatoes, potatoes and paprika; lauraceae, such as avocado, cinnamon and camphor; and tobacco, nuts, coffee, aubergines, sugar cane, tea, pepper, vines, hops, bananas, natural rubber plants and ornamentals.

Further areas of use of the active ingredients according to the invention are the protection of stored goods and storerooms and the protection of raw materials, and also in the hygiene sector, especially the protection of domestic animals and productive livestock against pests of the mentioned type The invention therefore relates also to pesticidal compositions, such as emulsifiable concentrates, suspension concentrates, directly sprayable or dilutable solutions, spreadable pastes, dilute emulsions, wettable powders, soluble powders, dispersible powders, wettable powders, dusts, granules and encapsulations in polymer substances, that comprise at least one of the active ingredients according to the invention, the choice of formulation being made in accordance with the intended objectives and the prevailing circumstances.

The active ingredient is used in those compositions in pure form, a solid active ingredient, for example, being used in a specific particle size, or preferably together with at least one of the adjuvants customary in formulation technology, such as extenders, e.g. solvents or solid carriers, or surface-active compounds (surfactants).

As formulation adjuvants there are used, for example, solid carriers, solvents, stabilisers, "slow release" adjuvants, colourings and optionally surface-active substances (surfactants). Suitable carriers and adjuvants include all substances customarily used in crop protection products, especially products for the control of slugs and snails. As adjuvants, such as solvents, solid carriers, surface-active compounds, non-ionic surfactants, cationic surfactants, anionic surfactants and further adjuvants in the compositions used according to the invention, there come into consideration, for example, those described in EP-A-736 252; they are included by reference in the subject matter of the present invention.

The compositions generally comprise from 0.1 to 99%, especially from 0.1 to 95%, of active ingredient and from 1 to 99.9%, especially from 5 to 99.9%, of at least one solid or liquid adjuvant, the composition generally including from 0 to 25%, especially from 0.1 to 20%, of surfactants (%=% by weight in each case). Whereas commercial products will preferably be formulated as concentrates, the end user will normally employ dilute formulations having considerably lower concentrations of active ingredient. Preferred compositions have especially the following compositions (%=percent by weight):

Emulsifiable Concentrates:

| active ingredient: | 1 to 95%, preferably 5 to 20% |
| --- | --- |
| surfactant: | 1 to 30%, preferably 10 to 20% |
| solvent: | 5 to 98%, preferably 70 to 85% |

Dusts:

| active ingredient: | 0.1 to 10%, preferably 0.1 to 1% |
| --- | --- |
| solid carrier: | 99.9 to 90%, preferably 99.9 to 99% |

Suspension Concentrates:

| active ingredient: | 5 to 75%, preferably 10 to 50% |
| --- | --- |
| water: | 94 to 24%, preferably 88 to 30% |
| surfactant: | 1 to 40%, preferably 2 to 30% |

Wettable Powders:

| active ingredient: | 0.5 to 90%, preferably 1 to 80% |
| --- | --- |
| surfactant: | 0.5 to 20%, preferably 1 to 15% |
| solid carrier: | 5 to 99%, preferably 15 to 98% |

Granules:

| active ingredient: | 0.5 to 30%, preferably 3 to 15% |
| --- | --- |
| solid carrier: | 99.5 to 70%, preferably 97 to 85% |

The action of the compounds according to the invention and the compositions comprising them against animal pests can be significantly broadened and adapted to the given circumstances by the addition of other insecticides, acaricides or nematicides. Suitable additives include, for example, members of the following classes of active ingredient: organophosphorus compounds, nitrophenols and derivatives, formamidines, ureas, carbamates, pyrethroids, chlorinated hydrocarbons, neonicotinoids and *Bacillus thuringiensis* preparations.

Examples of especially suitable mixing partners include: azamethiphos; chlorfenvinphos; cypermethrin, cypermethrin high-cis; cyromazine; diafenthiuron; diazinon; dichlorvos; dicrotophos; dicyclanil; fenoxycarb; fluazuron; furathiocarb; isazofos; iodfenphos; kinoprene; lufenuron; methacriphos; methidathion; monocrotophos; phosphamidon; profenofos; diofenolan; a compound obtainable from the *Bacillus thuringiensis* strain GC91 or from the strain NCTC11821; pymetrozine; bromopropylate; methoprene; disulfoton; quinalphos; tau-fluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; cyfluthrin; lambda-cyhalothrin; alpha-cypermethrin; zeta-cypermethrin; deltamethrin; diflubenzuron; endosulfan; ethiofencarb; fenitrothion; fenobucarb; fenvalerate; formothion; methiocarb; heptenophos; imidacloprid; isoprocarb; methamidophos; methomyl; mevinphos; parathion; parathion-methyl; phosalone; pirimicarb; propoxur; teflubenzuron; terbufos; triazamate; fenobucarb; tebufenozide; fipronil; beta-cyfluthrin; silafluofen; fenpyroximate; pyridaben; fenazaquin; pyriproxyfen; pyrimidifen; nitenpyram; acetamiprid; avermectin $B_1$ (abamectin); emamectin; emamectin benzoate; spinosad; a plant extract that is active against insects; a preparation that comprises nematodes and is active against insects; a preparation obtainable from *Bacillus subtilis*; a preparation that comprises fungi and is active against insects; a preparation that comprises viruses and is active against insects; chlorfenapyr; acephate; acrinathrin; alanycarb; alphamethrin; amitraz; AZ 60541; azinphos A; azinphos M; azocyclotin; bendiocarb; bensultap; betacyfluthrin; BPMC; brofenprox; bromophos A; bufencarb; butocarboxim; butylpyridaben; cadusafos; carbaryl; carbophenothion; chloethocarb; chlorethoxyfos; chlormephos; cis-resmethrin; clocythrin; clofentezine; cyanophos; cycloprothrin; cyhexatin; demeton M; demeton S; demeton-S-methyl; dichlofenthion; dicliphos; diethion; dimethoate; dimethylvinphos; dioxathion; edifenphos; esfenvalerate; ethion; ethofenprox; ethoprophos; etrimphos; fenamiphos; fernbutatin oxide; fenothiocarb; fenpropathrin; fenpyrad; fenthion; fluazinam; flucycloxuron; flucythrinate; flufenoxuron; flufenprox; fonophos; fosthiazate; fubfenprox; HCH; hexaflumuron; hexythiazox; IKI-220; iprobenfos; isofenphos; isoxathion; ivermectin; malathion; mecarbam; mesulfenphos; metaldehyde; metolcarb; milbemectin; moxidectin; naled; NC 184; omethoate; oxamyl; oxydemeton M; oxydeprofos; permethrin; phenthoate; phorate; phosmet; phoxim; pirimiphos M; pirimiphos E; promecarb; propaphos; prothiofos; prothoate; pyrachlophos; pyradaphenthion; pyresmethrin; pyrethrum; tebufenozide, salithion; sebufos; sulfotep; sulprofos; tebufenpyrad; tebupirimphos; tefluthrin; temephos; terbam; tetrachlorvinphos; thiacloprid; thiafenox; thiodicarb; thiofanox; thionazin; thuringiensin; tralomethrin; triarthene; triazophos; triazuron; trichlorfon; triflumuron; trimethacarb; vamidothion; xylylcarb; YI 5301/5302; zetamethrin; DPX-MP062—indoxacarb; methoxyfenozide; bifenazate; XMC (3,5-xylyl methylcarbamate); or the fungus pathogen *Metarhizium anisopliae*; more especially fipronil, thiamethoxam or lambda-cyhalothrin.

The compositions according to the invention may also comprise further solid or liquid adjuvants, such as stabilisers, e.g. vegetable oils or epoxidised vegetable oils (e.g. epoxidised coconut oil, rapeseed oil or soybean oil), antifoams, e.g. silicone oil, preservatives, viscosity regulators, binders and/or tackifiers as well as fertilisers or other active ingredients for obtaining special effects, e.g. acaricides, bactericides, fungicides, nematicides, molluscicides or selective herbicides.

The compositions according to the invention are prepared in known manner, in the absence of adjuvants, e.g. by grinding, sieving and/or compressing a solid active ingredient or mixture of active ingredients, for example to a certain particle size, and in the presence of at least one adjuvant, e.g. by intimately mixing and/or grinding the active ingredient or mixture of active ingredients with the adjuvant(s). The invention relates likewise to such processes for the preparation of the compositions according to the invention and to the use of the compounds of formula (I) in the preparation of such compositions.

The invention relates also to the methods of application of the compositions, i.e. the methods of controlling pests of the mentioned type, such as spraying, atomising, dusting, coating, dressing, scattering or pouring, which are selected in accordance with the intended objectives and the prevailing circumstances, and to the use of the compositions for controlling pests of the mentioned type. Typical rates of concentration are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha.

A preferred method of application in the area of crop protection is application to the foliage of the plants (foliar application), the frequency and the rate of application being dependent upon the risk of infestation by the pest in question. However, the active ingredient can also penetrate the plants through the roots (systemic action) when the locus of the plants is impregnated with a liquid formulation or when the active ingredient is incorporated in solid form into the locus of the plants, for example into the soil, e.g. in granular form (soil application). In the case of paddy rice crops, such granules may be applied in metered amounts to the flooded rice field.

The compositions according to the invention are also suitable for protecting plant propagation material, including genetically modified propagation material, e.g. seed, such as fruits, tubers or grains, or plant cuttings, against animal pests. The propagation material can be treated with the composition before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example to the seed furrow during sowing. The invention relates also to such methods of treating plant propagation material and to the plant propagation material so treated.

The following Examples serve to illustrate the invention. They do not limit the invention. Temperatures are given in degrees Celsius; mixing ratios of solvents are given in parts by volume.

PREPARATION EXAMPLES

Example P1

Preparation of (4-{3-[2,6-dichloro-4-(3,3-dichloroallyloxy)-phenoxy]-propoxy}-phenyl)-carbamic acid tert-butyl ester 1.69 g of azadicarboxylic acid diisopropyl ester are added dropwise at 0–5° C. to a solution of 1.97 g of triphenylphosphine in 60 ml of THF. After 30 minutes at 0–5° C., 2.5 g of 3-[2,6-dichloro-4-(3,3-dichloroallyloxy)-phenoxy]-propan-1-ol and 1.5 g of (4-hydroxy-phenyl)-carbamic acid tert-butyl ester dissolved in 30 ml of tetrahydrofuran are added dropwise. After being stirred for 24 hours at room temperature, the reaction mixture is concentrated and then purified over silica gel. (4-{3-[2,6-Dichloro-4-(3,3-dichloroallyloxy)-phenoxy]-propoxy}-phenyl)-carbamic acid tert-butyl ester (compound 1.6) is obtained.

Example P2

In a manner analogous to that described above it is also possible to prepare the further compounds of Tables 2 to 28 below.

TABLE A

Compounds of formula

TABLE A-continued

Compounds of formula

[Structure: R_9-C(=O)-N(R_5)-phenyl-C(=O)NH-[CH_2]_n-O-(2,6-dichlorophenyl)-O-CH_2-CH=C(X_1)(X_2)]

| No. | R₉ | R₅ |
|---|---|---|
| A.1 | H | H |
| A.2 | methoxy | H |
| A.3 | ethoxy | H |
| A.4 | propoxy | H |
| A.5 | butoxy | H |
| A.6 | pentyloxy | H |
| A.7 | hexyloxy | H |
| A.8 | isopropoxy | H |
| A.9 | isobutoxy | H |
| A.10 | isopentyloxy | H |
| A.11 | tert-butoxy | H |
| A.12 | 2,2-dimethylpropoxy | H |
| A.13 | vinyloxy | H |
| A.14 | allyloxy | H |
| A.15 | propargyloxy | H |
| A.16 | propen-2-yloxy | H |
| A.17 | benzyloxy | H |
| A.18 | 4-nitrobenzyloxy | H |
| A.19 | methyl | H |
| A.20 | ethyl | H |
| A.21 | propyl | H |
| A.22 | butyl | H |
| A.23 | pentyl | H |
| A.24 | hexyl | H |
| A.25 | isopropyl | H |
| A.26 | isobutyl | H |
| A.27 | isopentyl | H |
| A.28 | tert-butyl | H |
| A.29 | 2,2-dimethylpropyl | H |
| A.30 | cyclopropyl | H |
| A.31 | cyclobutyl | H |
| A.32 | cyclopentyl | H |
| A.33 | cyclohexyl | H |
| A.34 | trifluoromethyl | H |
| A.35 | pentafluoroethyl | H |
| A.36 | 4-trifluoromethylphenyl | H |
| A.37 | 4-trifluoromethylbenzyl | H |
| A.38 | 2-chloro-(1-chloromethyl-1-methyl)-ethyl | H |
| A.39 | 2-chloro-1,1-dimethyl-ethyl | H |
| A.40 | H | methyl |
| A.41 | methoxy | methyl |
| A.42 | ethoxy | methyl |
| A.43 | propoxy | methyl |
| A.44 | butoxy | methyl |
| A.45 | pentyloxy | methyl |
| A.46 | hexyloxy | methyl |
| A.47 | isopropoxy | methyl |
| A.48 | isobutoxy | methyl |
| A.49 | isopentyloxy | methyl |
| A.50 | tert-butoxy | methyl |
| A.51 | 2,2-dimethylpropoxy | methyl |
| A.52 | vinyloxy | methyl |
| A.53 | allyloxy | methyl |
| A.54 | propargyloxy | methyl |
| A.55 | propen-2-yloxy | methyl |
| A.56 | benzyloxy | methyl |
| A.57 | 4-nitrobenzyloxy | methyl |
| A.58 | methyl | methyl |
| A.59 | ethyl | methyl |
| A.60 | propyl | methyl |
| A.61 | butyl | methyl |
| A.62 | pentyl | methyl |
| A.63 | hexyl | methyl |
| A.64 | isopropyl | methyl |
| A.65 | isobutyl | methyl |

TABLE A-continued

| | Compounds of formula | |
|---|---|---|
| A.66 | isopentyl | methyl |
| A.67 | tert-butyl | methyl |
| A.68 | 2,2-dimethylpropyl | methyl |
| A.69 | cyclopropyl | methyl |
| A.70 | cyclobutyl | methyl |
| A.71 | cyclopentyl | methyl |
| A.72 | cyclohexyl | methyl |
| A.73 | trifluoromethyl | methyl |
| A.74 | pentafluoroethyl | methyl |
| A.75 | 4-trifluoromethylphenyl | methyl |
| A.76 | 4-trifluoromethylbenzyl | methyl |
| A.77 | 2-chloro-(1-chloromethyl-1-methyl)-ethyl | methyl |
| A.78 | 2-chloro-1,1-dimethyl-ethyl | methyl |
| A.79 | H | ethyl |
| A.80 | methoxy | ethyl |
| A.81 | ethoxy | ethyl |
| A.82 | propoxy | ethyl |
| A.83 | butoxy | ethyl |
| A.84 | pentyloxy | ethyl |
| A.85 | hexyloxy | ethyl |
| A.86 | isopropoxy | ethyl |
| A.87 | isobutoxy | ethyl |
| A.88 | isopentyloxy | ethyl |
| A.89 | tert-butoxy | ethyl |
| A.90 | 2,2-dimethylpropoxy | ethyl |
| A.91 | vinyloxy | ethyl |
| A.92 | allyloxy | ethyl |
| A.93 | propargyloxy | ethyl |
| A.94 | propen-2-yloxy | ethyl |
| A.95 | benzyloxy | ethyl |
| A.96 | 4-nitrobenzyloxy | ethyl |
| A.97 | methyl | ethyl |
| A.98 | ethyl | ethyl |
| A.99 | propyl | ethyl |
| A.100 | butyl | ethyl |
| A.101 | pentyl | ethyl |
| A.102 | hexyl | ethyl |
| A.103 | isopropyl | ethyl |
| A.104 | isobutyl | ethyl |
| A.105 | isopentyl | ethyl |
| A.106 | tert-butyl | ethyl |
| A.107 | 2,2-dimethylpropyl | ethyl |
| A.108 | cyclopropyl | ethyl |
| A.109 | cyclobutyl | ethyl |
| A.110 | cyclopentyl | ethyl |
| A.111 | cyclohexyl | ethyl |
| A.112 | trifluoromethyl | ethyl |
| A.113 | pentafluoroethyl | ethyl |
| A.114 | 4-trifluoromethylphenyl | ethyl |
| A.115 | 4-trifluoromethylbenzyl | ethyl |
| A.116 | 2-chloro-(1-chloromethyl-1-methyl)-ethyl | ethyl |
| A.117 | 2-chloro-1,1-dimethyl-ethyl | ethyl |
| A.118 | H | propyl |
| A.119 | methoxy | propyl |
| A.120 | ethoxy | propyl |
| A.121 | propoxy | propyl |
| A.122 | butoxy | propyl |
| A.123 | pentyloxy | propyl |
| A.124 | hexyloxy | propyl |
| A.125 | isopropoxy | propyl |
| A.126 | isobutoxy | propyl |
| A.127 | isopentyloxy | propyl |
| A.128 | tert-butoxy | propyl |
| A.129 | 2,2-dimethylpropoxy | propyl |
| A.130 | vinyloxy | propyl |
| A.131 | allyloxy | propyl |
| A.132 | propargyloxy | propyl |
| A.133 | propen-2-yloxy | propyl |
| A.134 | benzyloxy | propyl |
| A.135 | 4-nitrobenzyloxy | propyl |
| A.136 | methyl | propyl |
| A.137 | ethyl | propyl |
| A.138 | propyl | propyl |
| A.139 | butyl | propyl |
| A.140 | pentyl | propyl |
| A.141 | hexyl | propyl |
| A.142 | isopropyl | propyl |

TABLE A-continued

Compounds of formula

| | | |
|---|---|---|
| A.143 | isobutyl | propyl |
| A.144 | isopentyl | propyl |
| A.145 | tert-butyl | propyl |
| A.146 | 2,2-dimethylpropyl | propyl |
| A.147 | cyclopropyl | propyl |
| A.148 | cyclobutyl | propyl |
| A.149 | cyclopentyl | propyl |
| A.150 | cyclohexyl | propyl |
| A.151 | trifluoromethyl | propyl |
| A.152 | pentafluoroethyl | propyl |
| A.153 | 4-trifluoromethylphenyl | propyl |
| A.154 | 4-trifluoromethylbenzyl | propyl |
| A.155 | 2-chloro-(1-chloromethyl-1-methyl)-ethyl | propyl |
| A.156 | 2-chloro-1,1-dimethyl-ethyl | propyl |
| A.157 | H | allyl |
| A.158 | methoxy | allyl |
| A.159 | ethoxy | allyl |
| A.160 | propoxy | allyl |
| A.161 | butoxy | allyl |
| A.162 | pentyloxy | allyl |
| A.163 | hexyloxy | allyl |
| A.164 | isopropoxy | allyl |
| A.165 | isobutoxy | allyl |
| A.166 | isopentyloxy | allyl |
| A.167 | tert-butoxy | allyl |
| A.168 | 2,2-dimethylpropoxy | allyl |
| A.169 | vinyloxy | allyl |
| A.170 | allyloxy | allyl |
| A.171 | propargyloxy | allyl |
| A.172 | propen-2-yloxy | allyl |
| A.173 | benzyloxy | allyl |
| A.174 | 4-nitrobenzyloxy | allyl |
| A.175 | methyl | allyl |
| A.176 | ethyl | allyl |
| A.177 | propyl | allyl |
| A.178 | butyl | allyl |
| A.179 | pentyl | allyl |
| A.180 | hexyl | allyl |
| A.181 | isopropyl | allyl |
| A.182 | isobutyl | allyl |
| A.183 | isopentyl | allyl |
| A.184 | tert-butyl | allyl |
| A.185 | 2,2-dimethylpropyl | allyl |
| A.186 | cyclopropyl | allyl |
| A.187 | cyclobutyl | allyl |
| A.188 | cyclopentyl | allyl |
| A.189 | cyclohexyl | allyl |
| A.190 | trifluoromethyl | allyl |
| A.191 | pentafluoroethyl | allyl |
| A.192 | 4-trifluoromethylphenyl | allyl |
| A.193 | 4-trifluoromethylbenzyl | allyl |
| A.194 | 2-chloro-(1-chloromethyl-1-methyl)-ethyl | allyl |
| A.195 | 2-chloro-1,1-dimethyl-ethyl | allyl |
| A.196 | H | propargyl |
| A.197 | methoxy | propargyl |
| A.198 | ethoxy | propargyl |
| A.199 | propoxy | propargyl |
| A.200 | butoxy | propargyl |
| A.201 | pentyloxy | propargyl |
| A.202 | hexyloxy | propargyl |
| A.203 | isopropoxy | propargyl |
| A.204 | isobutoxy | propargyl |
| A.205 | isopentyloxy | propargyl |
| A.206 | tert-butoxy | propargyl |
| A.207 | 2,2-dimethylpropoxy | propargyl |
| A.208 | vinyloxy | propargyl |
| A.209 | allyloxy | propargyl |
| A.210 | propargyloxy | propargyl |
| A.211 | propen-2-yloxy | propargyl |
| A.212 | benzyloxy | propargyl |
| A.213 | 4-nitrobenzyloxy | propargyl |
| A.214 | methyl | propargyl |
| A.215 | ethyl | propargyl |
| A.216 | propyl | propargyl |
| A.217 | butyl | propargyl |
| A.218 | pentyl | propargyl |
| A.219 | hexyl | propargyl |

TABLE A-continued

Compounds of formula

| | | |
|---|---|---|
| A.220 | isopropyl | propargyl |
| A.221 | isobutyl | propargyl |
| A.222 | isopentyl | propargyl |
| A.223 | tert-butyl | propargyl |
| A.224 | 2,2-dimethylpropyl | propargyl |
| A.225 | cyclopropyl | propargyl |
| A.226 | cyclobutyl | propargyl |
| A.227 | cyclopentyl | propargyl |
| A.228 | cyclohexyl | propargyl |
| A.229 | trifluoromethyl | propargyl |
| A.230 | pentafluoroethyl | propargyl |
| A.231 | 4-trifluoromethylphenyl | propargyl |
| A.232 | 4-trifluoromethylbenzyl | propargyl |
| A.233 | 2-chloro-(1-chloromethyl-1-methyl)-ethyl | propargyl |
| A.234 | 2-chloro-1,1-dimethyl-ethyl | propargyl |
| A.235 | H | methoxy |
| A.236 | methoxy | methoxy |
| A.237 | ethoxy | methoxy |
| A.238 | propoxy | methoxy |
| A.239 | butoxy | methoxy |
| A.240 | pentyloxy | methoxy |
| A.241 | hexyloxy | methoxy |
| A.242 | isopropoxy | methoxy |
| A.243 | isobutoxy | methoxy |
| A.244 | isopentyloxy | methoxy |
| A.245 | tert-butoxy | methoxy |
| A.246 | 2,2-dimethylpropoxy | methoxy |
| A.247 | vinyloxy | methoxy |
| A.248 | allyloxy | methoxy |
| A.249 | propargyloxy | methoxy |
| A.250 | propen-2-yloxy | methoxy |
| A.251 | benzyloxy | methoxy |
| A.252 | 4-nitrobenzyloxy | methoxy |
| A.253 | methyl | methoxy |
| A.254 | ethyl | methoxy |
| A.255 | propyl | methoxy |
| A.256 | butyl | methoxy |
| A.257 | pentyl | methoxy |
| A.258 | hexyl | methoxy |
| A.259 | isopropyl | methoxy |
| A.260 | isobutyl | methoxy |
| A.261 | isopentyl | methoxy |
| A.262 | tert-butyl | methoxy |
| A.263 | 2,2-dimethylpropyl | methoxy |
| A.264 | cyclopropyl | methoxy |
| A.265 | cyclobutyl | methoxy |
| A.266 | cyclopentyl | methoxy |
| A.267 | cyclohexyl | methoxy |
| A.268 | trifluoromethyl | methoxy |
| A.269 | pentafluoroethyl | methoxy |
| A.270 | 4-trifluoromethylphenyl | methoxy |
| A.271 | 4-trifluoromethylbenzyl | methoxy |
| A.272 | 2-chloro-(1-chloromethyl-1-methyl)-ethyl | methoxy |
| A.273 | 2-chloro-1,1-dimethyl-ethyl | methoxy |
| A.274 | H | ethoxy |
| A.275 | methoxy | ethoxy |
| A.276 | ethoxy | ethoxy |
| A.277 | propoxy | ethoxy |
| A.278 | butoxy | ethoxy |
| A.279 | pentyloxy | ethoxy |
| A.280 | hexyloxy | ethoxy |
| A.281 | isopropoxy | ethoxy |
| A.282 | isobutoxy | ethoxy |
| A.283 | isopentyloxy | ethoxy |
| A.284 | tert-butoxy | ethoxy |
| A.285 | 2,2-dimethylpropoxy | ethoxy |
| A.286 | vinyloxy | ethoxy |
| A.287 | allyloxy | ethoxy |
| A.288 | propargyloxy | ethoxy |
| A.289 | propen-2-yloxy | ethoxy |
| A.290 | benzyloxy | ethoxy |
| A.291 | 4-nitrobenzyloxy | ethoxy |
| A.292 | methyl | ethoxy |
| A.293 | ethyl | ethoxy |
| A.294 | propyl | ethoxy |
| A.295 | butyl | ethoxy |
| A.296 | pentyl | ethoxy |

TABLE A-continued

Compounds of formula

| | | |
|---|---|---|
| A.297 | hexyl | ethoxy |
| A.298 | isopropyl | ethoxy |
| A.299 | isobutyl | ethoxy |
| A.300 | isopentyl | ethoxy |
| A.301 | tert-butyl | ethoxy |
| A.302 | 2,2-dimethylpropyl | ethoxy |
| A.303 | cyclopropyl | ethoxy |
| A.304 | cyclobutyl | ethoxy |
| A.305 | cyclopentyl | ethoxy |
| A.306 | cyclohexyl | ethoxy |
| A.307 | trifluoromethyl | ethoxy |
| A.308 | pentafluoroethyl | ethoxy |
| A.309 | 4-trifluoromethylphenyl | ethoxy |
| A.310 | 4-trifluoromethylbenzyl | ethoxy |
| A.311 | 2-chloro-(1-chloromethyl-1-methyl)-ethyl | ethoxy |
| A.312 | 2-chloro-1,1-dimethyl-ethyl | ethoxy |
| A.313 | H | methylcarbonyl |
| A.314 | methoxy | methylcarbonyl |
| A.315 | ethoxy | methylcarbonyl |
| A.316 | propoxy | methylcarbonyl |
| A.317 | butoxy | methylcarbonyl |
| A.318 | pentyloxy | methylcarbonyl |
| A.319 | hexyloxy | methylcarbonyl |
| A.320 | isopropoxy | methylcarbonyl |
| A.321 | isobutoxy | methylcarbonyl |
| A.322 | isopentyloxy | methylcarbonyl |
| A.323 | tert-butoxy | methylcarbonyl |
| A.324 | 2,2-dimethylpropoxy | methylcarbonyl |
| A.325 | vinyloxy | methylcarbonyl |
| A.326 | allyloxy | methylcarbonyl |
| A.327 | propargyloxy | methylcarbonyl |
| A.328 | propen-2-yloxy | methylcarbonyl |
| A.329 | benzyloxy | methylcarbonyl |
| A.330 | 4-nitrobenzyloxy | methylcarbonyl |
| A.331 | methyl | methylcarbonyl |
| A.332 | ethyl | methylcarbonyl |
| A.333 | propyl | methylcarbonyl |
| A.334 | butyl | methylcarbonyl |
| A.335 | pentyl | methylcarbonyl |
| A.336 | hexyl | methylcarbonyl |
| A.337 | isopropyl | methylcarbonyl |
| A.338 | isobutyl | methylcarbonyl |
| A.339 | isopentyl | methylcarbonyl |
| A.340 | tert-butyl | methylcarbonyl |
| A.341 | 2,2-dimethylpropyl | methylcarbonyl |
| A.342 | cyclopropyl | methylcarbonyl |
| A.343 | cyclobutyl | methylcarbonyl |
| A.344 | cyclopentyl | methylcarbonyl |
| A.345 | cyclohexyl | methylcarbonyl |
| A.346 | trifluoromethyl | methylcarbonyl |
| A.347 | pentafluoroethyl | methylcarbonyl |
| A.348 | 4-trifluoromethylphenyl | methylcarbonyl |
| A.349 | 4-trifluoromethylbenzyl | methylcarbonyl |
| A.350 | 2-chloro-(1-chloromethyl-1-methyl)-ethyl | methylcarbonyl |
| A.351 | 2-chloro-1,1-dimethyl-ethyl | methylcarbonyl |
| A.352 | H | ethylcarbonyl |
| A.353 | methoxy | ethylcarbonyl |
| A.354 | ethoxy | ethylcarbonyl |
| A.355 | propoxy | ethylcarbonyl |
| A.356 | butoxy | ethylcarbonyl |
| A.357 | pentyloxy | ethylcarbonyl |
| A.358 | hexyloxy | ethylcarbonyl |
| A.359 | isopropoxy | ethylcarbonyl |
| A.360 | isobutoxy | ethylcarbonyl |
| A.361 | isopentyloxy | ethylcarbonyl |
| A.362 | tert-butoxy | ethylcarbonyl |
| A.363 | 2,2-dimethylpropoxy | ethylcarbonyl |
| A.364 | vinyloxy | ethylcarbonyl |
| A.365 | allyloxy | ethylcarbonyl |
| A.366 | propargyloxy | ethylcarbonyl |
| A.367 | propen-2-yloxy | ethylcarbonyl |
| A.368 | benzyloxy | ethylcarbonyl |
| A.369 | 4-nitrobenzyloxy | ethylcarbonyl |
| A.370 | methyl | ethylcarbonyl |
| A.371 | ethyl | ethylcarbonyl |
| A.372 | propyl | ethylcarbonyl |
| A.373 | butyl | ethylcarbonyl |

TABLE A-continued

Compounds of formula

| | | |
|---|---|---|
| A.374 | pentyl | ethylcarbonyl |
| A.375 | hexyl | ethylcarbonyl |
| A.376 | isopropyl | ethylcarbonyl |
| A.377 | isobutyl | ethylcarbonyl |
| A.378 | isopentyl | ethylcarbonyl |
| A.379 | tert-butyl | ethylcarbonyl |
| A.380 | 2,2-dimethylpropyl | ethylcarbonyl |
| A.381 | cyclopropyl | ethylcarbonyl |
| A.382 | cyclobutyl | ethylcarbonyl |
| A.383 | cyclopentyl | ethylcarbonyl |
| A.384 | cyclohexyl | ethylcarbonyl |
| A.385 | trifluoromethyl | ethylcarbonyl |
| A.386 | pentafluoroethyl | ethylcarbonyl |
| A.387 | 4-trifluoromethylphenyl | ethylcarbonyl |
| A.388 | 4-trifluoromethylbenzyl | ethylcarbonyl |
| A.389 | 2-chloro-(1-chloromethyl-1-methyl)-ethyl | ethylcarbonyl |
| A.390 | 2-chloro-1,1-dimethyl-ethyl | ethylcarbonyl |
| A.391 | H | cyclopropylcarbonyl |
| A.392 | methoxy | cyclopropylcarbonyl |
| A.393 | ethoxy | cyclopropylcarbonyl |
| A.394 | propoxy | cyclopropylcarbonyl |
| A.395 | butoxy | cyclopropylcarbonyl |
| A.396 | pentyloxy | cyclopropylcarbonyl |
| A.397 | hexyloxy | cyciopropylcarbonyl |
| A.398 | isopropoxy | cyclopropylcarbonyl |
| A.399 | isobutoxy | cyclopropylcarbonyl |
| A.400 | isopentyloxy | cyclopropylcarbonyl |
| A.401 | tert-butoxy | cyclopropylcarbonyl |
| A.402 | 2,2-dimethylpropoxy | cyclopropylcarbonyl |
| A.403 | vinyloxy | cyclopropylcarbonyl |
| A.404 | allyloxy | cyclopropylcarbonyl |
| A.405 | propargyloxy | cyclopropylcarbonyl |
| A.406 | propen-2-yloxy | cyclopropylcarbonyl |
| A.407 | benzyloxy | cyclopropylcarbonyl |
| A.408 | 4-nitrobenzyloxy | cyclopropylcarbonyl |
| A.409 | methyl | cyclopropylcarbonyl |
| A.410 | ethyl | cyclopropylcarbonyl |
| A.411 | propyl | cyclopropylcarbonyl |
| A.412 | butyl | cyclopropylcarbonyl |
| A.413 | pentyl | cyclopropylcarbonyl |
| A.414 | hexyl | cyclopropylcarbonyl |
| A.415 | isopropyl | cyclopropylcarbonyl |
| A.416 | isobutyl | cyclopropylcarbonyl |
| A.417 | isopentyl | cyclopropylcarbonyl |
| A.418 | tert-butyl | cyclopropylcarbonyl |
| A.419 | 2,2-dimethylpropyl | cyclopropylcarbonyl |
| A.420 | cyclopropyl | cyclopropylcarbonyl |
| A.421 | cyclobutyl | cyclopropylcarbonyl |
| A.422 | cyclopentyl | cyclopropylcarbonyl |
| A.423 | cyclohexyl | cyclopropylcarbonyl |
| A.424 | trifluoromethyl | cyclopropylcarbonyl |
| A.425 | pentafluoroethyl | cyclopropylcarbonyl |
| A.426 | 4-trifluoromethylphenyl | cyclopropylcarbonyl |
| A.427 | 4-trifluoromethylbenzyl | cyclopropylcarbonyl |
| A.428 | 2-chloro-(1-chloromethyl-1-methyl)-ethyl | cyclopropylcarbonyl |
| A.429 | 2-chloro-1,1-dimethyl-ethyl | cyclopropylcarbonyl |
| A.430 | H | methoxycarbonyl |
| A.431 | methoxy | methoxycarbonyl |
| A.432 | ethoxy | methoxycarbonyl |
| A.433 | propoxy | methoxycarbonyl |
| A.434 | butoxy | methoxycarbonyl |
| A.435 | pentyloxy | methoxycarbonyl |
| A.436 | hexyloxy | methoxycarbonyl |
| A.437 | isopropoxy | methoxycarbonyl |
| A.438 | isobutoxy | methoxycarbonyl |
| A.439 | isopentyloxy | methoxycarbonyl |
| A.440 | tert-butoxy | methoxycarbonyl |
| A.441 | 2,2-dimethylpropoxy | methoxycarbonyl |
| A.442 | vinyloxy | methoxycarbonyl |
| A.443 | allyloxy | methoxycarbonyl |
| A.444 | propargyloxy | methoxycarbonyl |
| A.445 | propen-2-yloxy | methoxycarbonyl |
| A.446 | benzyloxy | methoxycarbonyl |
| A.447 | 4-nitrobenzyloxy | methoxycarbonyl |
| A.448 | methyl | methoxycarbonyl |
| A.449 | ethyl | methoxycarbonyl |
| A.450 | propyl | methoxycarbonyl |

TABLE A-continued

Compounds of formula

| | | |
|---|---|---|
| A.451 | butyl | methoxycarbonyl |
| A.452 | pentyl | methoxycarbonyl |
| A.453 | hexyl | methoxycarbonyl |
| A.454 | isopropyl | methoxycarbonyl |
| A.455 | isobutyl | methoxycarbonyl |
| A.456 | isopentyl | methoxycarbonyl |
| A.457 | tert-butyl | methoxycarbonyl |
| A.458 | 2,2-dimethylpropyl | methoxycarbonyl |
| A.459 | cyclopropyl | methoxycarbonyl |
| A.460 | cyclobutyl | methoxycarbonyl |
| A.461 | cyclopentyl | methoxycarbonyl |
| A.462 | cyclohexyl | methoxycarbonyl |
| A.463 | trifluoromethyl | methoxycarbonyl |
| A.464 | pentafluoroethyl | methoxycarbonyl |
| A.465 | 4-trifluoromethylphenyl | methoxycarbonyl |
| A.466 | 4-trifluoromethylbenzyl | methoxycarbonyl |
| A.467 | 2-chloro-(1-chloromethyl-1-methyl)-ethyl | methoxycarbonyl |
| A.468 | 2-chloro-1,1-dimethyl-ethyl | methoxycarbonyl |
| A.469 | H | ethoxycarbonyl |
| A.470 | methoxy | ethoxycarbonyl |
| A.471 | ethoxy | ethoxycarbonyl |
| A.472 | propoxy | ethoxycarbonyl |
| A.473 | butoxy | ethoxycarbonyl |
| A.474 | pentyloxy | ethoxycarbonyl |
| A.475 | hexyloxy | ethoxycarbonyl |
| A.476 | isopropoxy | ethoxycarbonyl |
| A.477 | isobutoxy | ethoxycarbonyl |
| A.478 | isopentyloxy | ethoxycarbonyl |
| A.479 | tert-butoxy | ethoxycarbonyl |
| A.480 | 2,2-dimethylpropoxy | ethoxycarbonyl |
| A.481 | vinyloxy | ethoxycarbonyl |
| A.482 | allyloxy | ethoxycarbonyl |
| A.483 | propargyloxy | ethoxycarbonyl |
| A.484 | propen-2-yloxy | ethoxycarbonyl |
| A.485 | benzyloxy | ethoxycarbonyl |
| A.486 | 4-nitrobenzyloxy | ethoxycarbonyl |
| A.487 | methyl | ethoxycarbonyl |
| A.488 | ethyl | ethoxycarbonyl |
| A.489 | propyl | ethoxycarbonyl |
| A.490 | butyl | ethoxycarbonyl |
| A.491 | pentyl | ethoxycarbonyl |
| A.492 | hexyl | ethoxycarbonyl |
| A.493 | isopropyl | ethoxycarbonyl |
| A.494 | isobutyl | ethoxycarbonyl |
| A.495 | isopentyl | ethoxycarbonyl |
| A.496 | tert-butyl | ethoxycarbonyl |
| A.497 | 2,2-dimethylpropyl | ethoxycarbonyl |
| A.498 | cyclopropyl | ethoxycarbonyl |
| A.499 | cyclobutyl | ethoxycarbonyl |
| A.500 | cyclopentyl | ethoxycarbonyl |
| A.501 | cyclohexyl | ethoxycarbonyl |
| A.502 | trifluoromethyl | ethoxycarbonyl |
| A.503 | pentafluoroethyl | ethoxycarbonyl |
| A.504 | 4-trifluoromethylphenyl | ethoxycarbonyl |
| A.505 | 4-trifluoromethylbenzyl | ethoxycarbonyl |
| A.506 | 2-chloro-(1-chloromethyl-1-methyl)-ethyl | ethoxycarbonyl |
| A.507 | 2-chloro-1,1-dimethyl-ethyl | ethoxycarbonyl |

TABLE 1

Compounds of formula

[Structure: R6(R5)N-C6H4-O-(CH2)3-O-[2,6-dichloro-4-(OCH2CH=CCl2)phenyl]]

| No. | R5 | R6 | ¹H-NMR (CDCl₃) 300 MHz |
|---|---|---|---|
| 1.1 | H | H | 2.26 (m, 2H), 3.40 (s, NH₂), 4.10–4.22 (m, 6H), 4.59 (d, 2H), 6.12 (t, 1H), 6.63 (d, 2H), 6.78 (d, 2H), 6.82 (s, 2H) |
| 1.2 | methyl | methyl | 2.26 (m, 2H), 2.88 (s, 6H) 4.10–4.22 (m, 4H), 4.58 (d, 2H), 6.10 (t, 1H), 6.74 (d, 2H), 6.82 (s, 2H), 6.88 (d, 2H) |
| 1.3 | methoxycarbonyl | H | 2.28 (m, 2H), 3.76 (s, 3H), 4.13 (t, 2H), 4.22 (t, 2H), 4.58 (d, 2H), 6.10 (t, 1H), 6.50 (s, NH), 6.82 (s, 2H), 6.88 (d, 2H), 7.28 (d, 2H) |
| 1.4 | ethoxycarbonyl | H | 1.31 (t, 3H), 2.28 (m, 2H), 4.17 (t, 2H), 4.20–4.30 (t, 2H + q, 2H), 4.58 (d, 2H), 6.12 (t, 1H), 6.47 (s, NH), 6.85 (s, 2H), 6.88 (d, 2H), 7.28 (d, 2H) |
| 1.5 | isopropoxycarbonyl | H | 1.30 (d, 6H), 2.28 (m, 2H), 4.15 (t, 2H), 4.23 (t, 2H), 4.58 (d, 2H), 5.02 (m, 1H), 6.11 (t, 1H), 6.40 (s, NH), 6.85 (s, 2H), 6.89 (d, 2H), 7.28 (d, 2H) |
| 1.6 | tert-butyloxy-carbonyl | H | 1.50 (s, 9H), 2.28 (m, 2H), 4.13 (t, 2H), 4.21 (t, 2H), 4.58 (d, 2H), 6.12 (t, 1H), 6.37 (s, NH), 6.82 (s, 2H), 6.88 (d, 2H), 7.28 (d, 2H) |
| 1.7 | 2,2-dimethyl-propyloxycarbonyl | H | 0.98 (s, 9H), 2.29 (m, 2H), 3.38 (t, 2H), 4.16 (t, 2H), 4.23 (t, 2H), 4.58 (d, 2H), 6.11 (t, 1H), 6.50 (s, NH), 6.82 (s, 2H), 6.89 (d, 2H), 7.28 (d, 2H) |
| 1.8 | vinyloxycarbonyl | H | 2.29 (m, 2H), 4.17 (t, 2H), 4.24 (t, 2H), 4.52 (d, 1H), 4.58 (d, 2H) 4.83 (d, 1H), 6.12 (t, 1H), 6.63 (s, NH), 6.86 (s, 2H), 6.92 (d, 2H), 7.25–7.37 (m, 2H + 1H) |
| 1.9 | allyloxycarbonyl | H | 2.29 (m, 2H), 4.17 (t, 2H), 4.23 (t, 2H), 4.59 (d, 2H) 4.66 (d, 2H), 5.27 (d, 1H), 5.37 (d, 1H) 5.9–6.09 (m, 1H), 6.12 (t, 1H), 6.51 (s, NH), 6.85 (s, 2H), 6.90 (d, 2H), 7.29 (d, 2H) |
| 1.10 | propargyloxy-carbonyl | H | 2.28 (m, 2H), 2.51 (s, 1H), 4.15 (t, 2H), 4.25 (t, 2H), 4.60 (d, 2H), 4.80 (s, 2H), 6.11 (t, 1H), 6.63 (s, NH), 6.88 (s, 2H), 6.90 (d, 2H), 7.30 (d, 2H) |
| 1.11 | propen-2-yloxy-carbonyl | H | 2.00 (s, 3H), 2.29 (m, 2H), 4.17 (t, 2H), 4.23 (t, 2H), 4.52 (dd, 1H), 4.49 (d, 2H) 4.72 (s, 1H), 4.80 (s, 1H) 6.12 (t, 1H), 6.60 (s, NH), 6.83 (s, 2H), 6.91 (d, 2H), 7.32 (d, 2H) |
| 1.12 | benzyloxycarbonyl | H | 2.28 (m, 2H), 4.17 (t, 2H), 4.25 (t, 2H), 4.60 (d, 2H), 5.19 (s, 2H), 6.12 (t, 1H), 6.54 (s, NH), 6.83 (s, 2H), 6.90 (d, 2H), 7.28–7.45 (m, 7H) |
| 1.13 | 4-nitrobenzyloxy-carbonyl | H | 2.28 (m, 2H), 4.13 (t, 2H), 4.23 (t, 2H), 4.59 (d, 2H), 5.30 (s, 2H), 6.12 (t, 1H), 6.62 (s, NH), 6.83 (s, 2H), 6.90 (d, 2H), 7.39 (d, 2H), 7.57 (d, 2H), 8.23 (d, 2H) |

TABLE 1-continued

Compounds of formula

[Structure: R6(R5)N-C6H4-O-(CH2)3-O-[2,6-dichloro-4-(OCH2CH=CCl2)phenyl]]

| No. | R5 | R6 | ¹H-NMR (CDCl₃) 300 MHz |
|---|---|---|---|
| 1.14 | methylcarbonyl | H | 2.18 (s, 3H), 2.29 (m, 2H), 4.13 (t, 2H), 4.23 (t, 2H), 4.58 (d, 2H), 6.12 (t, 1H), 6.83 (s, 2H), 6.90 (d, 2H), 7.03 (s, NH), 7.40 (d, 2H) |
| 1.15 | 4-trifluoromethyl-carbonyl | H | 2.39 (m, 2H), 4.17 (t, 2H), 4.28 (t, 2H), 4.58 (d, 2H), 6.12 (t, 1H), 6.83 (s, 2H), 6.94 (d, 2H), 7.47 (d, 2H), 7.79 (s, NH) |
| 1.16 | 4-trifluoromethyl-phenyl-carbonyl | H | 2.29 (m, 2H), 4.16 (t, 2H), 4.28 (t, 2H), 4.58 (d, 2H), 6.11 (t, 1H), 6.83 (s, 2H), 6.93 (d, 2H), 7.53 (d, 2H), 7.72 (d, 2H), 7.88 (s, NH), 7.98 (d, 2H) |
| 1.17 | 4-trifluoromethyl-benzyl-carbonyl | H | 2.25 (m, 2H), 3.77 (s, 2H), 4.13 (t, 2H), 4.21 (t, 2H), 4.58 (d, 2H), 6.11 (t, 1H), 6.82 (s, 2H), 6.87 (d, 2H), 7.18 (s, NH), 7.33 (d, 2H), 7.48 (d, 2H), 7.63 (d, 2H) |
| 1.18 | 2-chloro-1,1-di-methyl-ethyl-carbonyl | H | 1.40 (s, 6H), 2.29 (m, 2H), 3.70 (s, 2H), 4.13 (t, 2H), 4.23 (t, 2H), 4.57 (d, 2H), 6.10 (t, 1H), 6.82 (s, 2H), 6.90 (d, 2H), 7.37–7.45 (d, 2H + s, NH) |

Table 2: Compounds of general formula (Ia) wherein $X_1$ and $X_2$ are fluorine and n is 2, and the combination of substituents $R_5$ and $R_9$ for each compound corresponds to a line A.1 to A.507 of Table A.

Table 3: Compounds of general formula (Ib) wherein $X_1$ and $X_2$ are fluorine and n is 2, and the combination of substituents $R_5$ and $R_9$ for each compound corresponds to a line A.1 to A.507 of Table A.

Table 4: Compounds of general formula (Ic) wherein $X_1$ and $X_2$ are fluorine and n is 2, and the combination of substituents $R_5$ and $R_9$ for each compound corresponds to a line A.1 to A.507 of Table A.

Table 5: Compounds of general formula (Ia) wherein $X_1$ and $X_2$ are fluorine and n is 3, and the combination of substituents $R_5$ and $R_9$ for each compound corresponds to a line A.1 to A.507 of Table A.

Table 6: Compounds of general formula (Ib) wherein $X_1$ and $X_2$ are fluorine and n is 3, and the combination of substituents $R_5$ and $R_9$ for each compound corresponds to a line A.1 to A.507 of Table A.

Table 7: Compounds of general formula (Ic) wherein $X_1$ and $X_2$ are fluorine and n is 3, and the combination of substituents $R_5$ and $R_9$ for each compound corresponds to a line A.1 to A.507 of Table A.

Table 8: Compounds of general formula (Ia) wherein $X_1$ and $X_2$ are fluorine and n is 4, and the combination of substituents $R_5$ and $R_9$ for each compound corresponds to a line A.1 to A.507 of Table A.

Table 9: Compounds of general formula (Ib) wherein $X_1$ and $X_2$ are fluorine and n is 4, and the combination of substituents $R_5$ and $R_9$ for each compound corresponds to a line A.1 to A.507 of Table A.

Table 10: Compounds of general formula (Ic) wherein $X_1$ and $X_2$ are fluorine and n is 4, and the combination of substituents $R_5$ and $R_9$ for each compound corresponds to a line A.1 to A.507 of Table A.

Table 11: Compounds of general formula (Ia) wherein $X_1$ and $X_2$ are chlorine and n is 2, and the combination of substituents $R_5$ and $R_9$ for each compound corresponds to a line A.1 to A.507 of Table A.

Table 12: Compounds of general formula (Ib) wherein $X_1$ and $X_2$ are chlorine and n is 2, and the combination of substituents $R_5$ and $R_9$ for each compound corresponds to a line A.1 to A.507 of Table A.

Table 13: Compounds of general formula (Ic) wherein $X_1$ and $X_2$ are chlorine and n is 2, and the combination of substituents $R_5$ and $R_9$ for each compound corresponds to a line A.1 to A.507 of Table A.

Table 14: Compounds of general formula (Ia) wherein $X_1$ and $X_2$ are chlorine and n is 3, and the combination of substituents $R_5$ and $R_9$ for each compound corresponds to a line A.1 to A.507 of Table A.

Table 15: Compounds of general formula (Ib) wherein $X_1$ and $X_2$ are chlorine and n is 3, and the combination of substituents $R_5$ and $R_9$ for each compound corresponds to a line A.1 to A.507 of Table A.

Table 16: Compounds of general formula (Ic) wherein $X_1$ and $X_2$ are chlorine and n is 3, and the combination of substituents $R_5$ and $R_9$ for each compound corresponds to a line A.1 to A.507 of Table A.

Table 17: Compounds of general formula (Ia) wherein $X_1$ and $X_2$ are chlorine and n is 4, and the combination of substituents $R_5$ and $R_9$ for each compound corresponds to a line A.1 to A.507 of Table A.

Table 18: Compounds of general formula (Ib) wherein $X_1$ and $X_2$ are chlorine and n is 4, and the combination of substituents $R_5$ and $R_9$ for each compound corresponds to a line A.1 to A.507 of Table A.

Table 19: Compounds of general formula (Ic) wherein $X_1$ and $X_2$ are chlorine and n is 4, and the combination of substituents $R_5$ and $R_9$ for each compound corresponds to a line A.1 to A.507 of Table A.

Table 20: Compounds of general formula (Ia) wherein $X_1$ and $X_2$ are bromine and n is 2, and the combination of substituents $R_5$ and $R_9$ for each compound corresponds to a line A.1 to A.507 of Table A.

Table 21: Compounds of general formula (Ib) wherein $X_1$ and $X_2$ are bromine and n is 2, and the combination of substituents $R_5$ and $R_9$ for each compound corresponds to a line A.1 to A.507 of Table A.

Table 22: Compounds of general formula (Ic) wherein $X_1$ and $X_2$ are bromine and n is 2, and the combination of substituents $R_5$ and $R_9$ for each compound corresponds to a line A.1 to A.507 of Table A.

Table 23: Compounds of general formula (Ia) wherein $X_1$ and $X_2$ are bromine and n is 3, and the combination of substituents $R_5$ and $R_9$ for each compound corresponds to a line A.1 to A.507 of Table A.

Table 24: Compounds of general formula (Ib) wherein $X_1$ and $X_2$ are bromine and n is 3, and the combination of substituents $R_5$ and $R_9$ for each compound corresponds to a line A.1 to A.507 of Table A.

Table 25: Compounds of general formula (Ic) wherein $X_1$ and $X_2$ are bromine and n is 3, and the combination of substituents $R_5$ and $R_9$ for each compound corresponds to a line A.1 to A.507 of Table A.

Table 26: Compounds of general formula (Ia) wherein $X_1$ and $X_2$ are bromine and n is 4, and the combination of substituents $R_5$ and $R_9$ for each compound corresponds to a line A.1 to A.507 of Table A.

Table 27: Compounds of general formula (Ib) wherein $X_1$ and $X_2$ are bromine and n is 4, and the combination of substituents $R_5$ and $R_9$ for each compound corresponds to a line A.1 to A.507 of Table A.

Table 28: Compounds of general formula (Ic) wherein $X_1$ and $X_2$ are bromine and n is 4, and the combination of substituents $R_5$ and $R_9$ for each compound corresponds to a line A.1 to A.507 of Table A.

Preparation Example P3

Preparation of 3-(4-{3-[2,6-dichloro-4-(3,3-dichloroallyloxy)-phenoxy]-propoxy}-phenyl)-oxazolidin-2-one 7 mg of copper(I) iodide, 2 mg of ethylenediamine and 155 mg of tripotassium phosphate are added, under argon, to a solution of 200 mg of 1,3-dichloro-5-(3,3-dichloro-allyloxy)-2-[3-(4-iodophenoxy)-propoxy]-benzene and 38 mg of 2-oxazolidinone in 4 ml of dioxane. After 17 hours at 110° C. the reaction mixture is filtered and concentrated. Purification over silica gel yields the title compound (compound 29.3).

Example P4

In a manner analogous to that described above it is also possible to prepare the further compounds of Tables 29 to 56 below.

TABLE 29

Compounds of formula

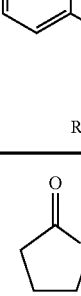

| No. | R | $^1$H-NMR (CDCl$_3$) 300 MHz |
|---|---|---|
| 29.1 | 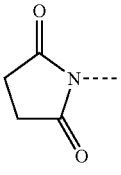 | 2.13 (m, 2H), 2.28 (m, 2H), 2.59 (t, 2H), 3.82 (t, 2H), 4.14 (t, 2H), 4.25 (t, 2H), 4.58 (d, 2H), 6.11 (t, 1H), 6.82 (s, 2H), 6.92 (d, 2H), 7.50 (d, 2H) |
| 29.2 | 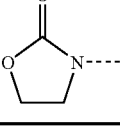 | 2.29 (m, 2H), 2.89 (s, 4H), 4.13 (t, 2H), 4.28 (t, 2H), 4.58 (d, 2H), 6.10 (t, 1H), 6.82 (s, 2H), 7.01 (d, 2H), 7.18 (d, 2H) |
| 29.3 | | 2.29 (m, 2H), 4.02 (t, 2H), 4.15 (t, 2H), 4.25 (t, 2H), 4.47 (t, 2H), 4.58 (d, 2H), 6.11 (t, 1H), 6.82 (s, 2H), 6.93 (d, 2H), 7.43 (d, 2H) |

TABLE B

Compounds of formulae

R—⟨C₆H₃⟩—O—[CH₂]n—O—⟨C₆H₂Cl₂⟩—O—CH₂—CH=C(X₁)(X₂)   (Id)

R—⟨C₆H₄⟩—C(=O)O—[CH₂]n—O—⟨C₆H₂Cl₂⟩—O—CH₂—CH=C(X₁)(X₂),   (Ie)

and

R—⟨C₆H₄⟩—C(=O)NH—[CH₂]n—O—⟨C₆H₂Cl₂⟩—O—CH₂—CH=C(X₁)(X₂)   (If)

| No. | R |
|---|---|
| B.1 | 3-(oxazolidin)-yl-2-one |
| B.2 | 3-(4-methyl-oxazolidin)-yl-2-one |
| B.3 | 3-(4-ethyl-oxazolidin)-yl-2-one |
| B.4 | 3-(4-propyl-oxazolidin)-yl-2-one |
| B.5 | 3-(4,4-dimethyl-oxazolidin)-yl-2-one |
| B.6 | 3-(4,4-diethyl-oxazolidin)-yl-2-one |
| B.7 | 3-(5-methyl-oxazolidin)-yl-2-one |
| B.8 | 3-(5-ethyl-oxazolidin)-yl-2-one |
| B.9 | 3-(5-propyl-oxazolidin)-yl-2-one |
| B.10 | 3-(5-cyclopropyl-oxazolidinone |
| B.11 | 3-(5-isopropyl-oxazolidin)-yl-2-one |
| B.12 | 3-(5-isobutyl-oxazolidin)-yl-2-one |
| B.13 | 3-(5-allyl-oxazolidin)-yl-2-one |
| B.14 | 3-(5-methoxymethyl-oxazolidin)-yl-2-one |
| B.15 | 3-(5-ethoxymethyl-oxazolidin)-yl-2-one |
| B.16 | 3-(5-propoxymethyl-oxazolidin)-yl-2-one |
| B.17 | 3-(5-cyclopropoxymethyl-oxazolidin)-yl-2-one |
| B.18 | 3-(5-isopropoxymethyl-oxazolidin)-yl-2-one |
| B.19 | 3-(5-isobutoxymethyl-oxazolidin)-yl-2-one |
| B.20 | 3-(5-allyloxymethyl-oxazolidin)-yl-2-one |
| B.21 | 3-(5-propargyloxymethyl-oxazolidin)-yl-2-one |
| B.22 | 3-(5,5-dimethyl-oxazolidin)-yl-2-one |
| B.23 | 3-(5,5-diethyl-oxazolidin)-yl-2-one |
| B.24 | 1-(pyrrolidin)-yl-2-one |
| B.25 | 1-(3-methyl-pyrrolidin)-yl-2-one |
| B.26 | 1-(3-ethyl-pyrrolidin)-yl-2-one |
| B.27 | 1-(3-propyl-pyrrolidin)-yl-2-one |
| B.28 | 1-(3-cyclopropyl-pyrrolidin)-yl-2-one |
| B.29 | 1-(3-isopropyl-pyrrolidin)-yl-2-one |
| B.30 | 1-(3-isobutyl-pyrrolidin)-yl-2-one |
| B.31 | 1-(3-allyl-pyrrolidin)-yl-2-one |
| B.32 | 1-(3-methoxymethyl-pyrrolidin)-yl-2-one |
| B.33 | 1-(3-ethoxymethyl-pyrrolidin)-yl-2-one |
| B.34 | 1-(3-propoxymethyl-pyrrolidin)-yl-2-one |
| B.35 | 1-(3-cyclopropoxymethyl-pyrrolidin)-yl-2-one |
| B.36 | 1-(3-isopropoxymethyl-pyrrolidin)-yl-2-one |
| B.37 | 1-(3-isobutoxymethyl-pyrrolidin)-yl-2-one |
| B.38 | 1-(3-allyloxymethyl-pyrrolidin)-yl-2-one |
| B.39 | 1-(3,3-dimethyl-pyrrolidin)-yl-2-one |
| B.40 | 1-(3,3-diethyl-pyrrolidin)-yl-2-one |
| B.41 | 1-(5-methyl-pyrrolidin)-yl-2-one |
| B.42 | 1-(5-ethyl-pyrrolidin)-yl-2-one |
| B.43 | 1-(5-propyl-pyrrolidin-2-one |
| B.44 | 1-(5-cyclopropyl-pyrrolidin)-yl-2-one |
| B.45 | 1-(5-isopropyl-pyrrolidin)-yl-2-one |
| B.46 | 1-(5-isobutyl-pyrrolidin)-yl-2-one |
| B.47 | 1-(5-allyl-pyrrolidin)-yl-2-one |
| B.48 | 1-(5-methoxymethyl-pyrrolidin)-yl-2-one |

TABLE B-continued

Compounds of formulae

| B.49 | 1-(5-ethoxymethyl-pyrrolidin)-yl-2-one |
|---|---|
| B.50 | 1-(5-propoxymethyl-pyrrolidin)-yl-2-one |
| B.51 | 1-(5-cyclopropoxymethyl-pyrrolidin)-yl-2-one |
| B.52 | 1-(5-isopropoxymethyl-pyrrolidin)-yl-2-one |
| B.53 | 1-(5-isobutoxymethyl-pyrrolidin)-yl-2-one |
| B.54 | 1-(5-allyloxymethyl-pyrrolidin)-yl-2-one |
| B.55 | 1-(5,5-dimethyl-pyrrolidin)-yl-2-one |
| B.56 | 1-(5,5-diethyl-pyrrolidin)-yl-2-one |
| B.57 | 1-(pyrrolidin)-yl-2,5-dione |
| B.58 | 1-(3-methyl-pyrrolidin)-yl-2,5-dione |
| B.59 | 1-(3-ethyl-pyrrolidin)-yl-2,5-dione |
| B.60 | 1-(3-propyl-pyrrolidin)-yl-2,5-dione |
| B.61 | 1-(3-cyclopropyl-pyrrolidin)-yl-2,5-dione |
| B.62 | 1-(3-isopropyl-pyrrolidin)-yl-2,5-dione |
| B.63 | 1-(3-isobutyl-pyrrolidin)-yl-2,5-dione |
| B.64 | 1-(3-allyl-pyrrolidin)-yl-2,5-dione |
| B.65 | 1-(3-methoxymethyl-pyrrolidin)-yl-2,5-dione |
| B.66 | 1-(3-ethoxymethyl-pyrrolidin)-yl-2,5-dione |
| B.67 | 1-(3-propoxymethyl-pyrrolidin)-yl-2,5-dione |
| B.68 | 1-(3-cyclopropoxymethyl-pyrrolidin)-yl-2,5-dione |
| B.69 | 1-(3-isopropoxymethyl-pyrrolidin)-yl-2,5-dione |
| B.70 | 1-(3-isobutoxymethyl-pyrrolidin)-yl-2,5-dione |
| B.71 | 1-(3-allyloxymethyl-pyrrolidin)-yl-2,5-dione |
| B.72 | 1-(3,3-dimethyl-pyrrolidin)-yl-2,5-dione |
| B.73 | 1-(3,3-diethyl-pyrrolidin)-yl-2,5-dione |

Table 30: Compounds of general formula (Id) wherein $X_1$ and $X_2$ are fluorine and n is 2, and the substituent R for each compound corresponds to a line B.1 to B.73 of Table B.

Table 31: Compounds of general formula (Ie) wherein $X_1$ and $X_2$ are fluorine and n is 2, and the substituent R for each compound corresponds to a line B.1 to B.73 of Table B.

Table 32: Compounds of general formula (If) wherein $X_1$ and $X_2$ are fluorine and n is 2, and the substituent R for each compound corresponds to a line B.1 to B.73 of Table B.

Table 33: Compounds of general formula (Id) wherein $X_1$ and $X_2$ are fluorine and n is 3, and the substituent R for each compound corresponds to a line B.1 to B.73 of Table B.

Table 34: Compounds of general formula (Ie) wherein $X_1$ and $X_2$ are fluorine and n is 3, and the substituent R for each compound corresponds to a line B.1 to B.73 of Table B.

Table 35: Compounds of general formula (If) wherein $X_1$ and $X_2$ are fluorine and n is 3, and the substituent R for each compound corresponds to a line B.1 to B.73 of Table B.

Table 36: Compounds of general formula (Id) wherein $X_1$ and $X_2$ are fluorine and n is 4, and the substituent R for each compound corresponds to a line B.1 to B.73 of Table B.

Table 37: Compounds of general formula (Ie) wherein $X_1$ and $X_2$ are fluorine and n is 4, and the substituent R for each compound corresponds to a line B.1 to B.73 of Table B.

Table 38: Compounds of general formula (If) wherein $X_1$ and $X_2$ are fluorine and n is 4, and the substituent R for each compound corresponds to a line B.1 to B.73 of Table B.

Table 39: Compounds of general formula (Id) wherein $X_1$ and $X_2$ are chlorine and n is 2, and the substituent R for each compound corresponds to a line B.1 to B.73 of Table B.

Table 40: Compounds of general formula (Ie) wherein $X_1$ and $X_2$ are chlorine and n is 2, and the substituent R for each compound corresponds to a line B.1 to B.73 of Table B.

Table 41: Compounds of general formula (If) wherein $X_1$ and $X_2$ are chlorine and n is 2, and the substituent R for each compound corresponds to a line B.1 to B.73 of Table B.

Table 42: Compounds of general formula (Id) wherein $X_1$ and $X_2$ are chlorine and n is 3, and the substituent R for each compound corresponds to a line B.1 to B.73 of Table B.

Table 43: Compounds of general formula (Ie) wherein $X_1$ and $X_2$ are chlorine and n is 3, and the substituent R for each compound corresponds to a line B.1 to B.73 of Table B.

Table 44: Compounds of general formula (If) wherein $X_1$ and $X_2$ are chlorine and n is 3, and the substituent R for each compound corresponds to a line B.1 to B.73 of Table B.

Table 45: Compounds of general formula (Id) wherein $X_1$ and $X_2$ are chlorine and n is 4, and the substituent R for each compound corresponds to a line B.1 to B.73 of Table B.

Table 46: Compounds of general formula (Ie) wherein $X_1$ and $X_2$ are chlorine and n is 4, and the substituent R for each compound corresponds to a line B.1 to B.73 of Table B.

Table 47: Compounds of general formula (If) wherein $X_1$ and $X_2$ are chlorine and n is 4, and the substituent R for each compound corresponds to a line B.1 to B.73 of Table B.

Table 48: Compounds of general formula (Id) wherein $X_1$ and $X_2$ are bromine and n is 2, and the substituent R for each compound corresponds to a line B.1 to B.73 of Table B.

Table 49: Compounds of general formula (Ie) wherein $X_1$ and $X_2$ are bromine and n is 2, and the substituent R for each compound corresponds to a line B.1 to B.73 of Table B.

Table 50: Compounds of general formula (If) wherein $X_1$ and $X_2$ are bromine and n is 2, and the substituent R for each compound corresponds to a line B.1 to B.73 of Table B.

Table 51: Compounds of general formula (Id) wherein $X_1$ and $X_2$ are bromine and n is 3, and the substituent R for each compound corresponds to a line B.1 to B.73 of Table B.

Table 52: Compounds of general formula (Ie) wherein $X_1$ and $X_2$ are bromine and n is 3, and the substituent R for each compound corresponds to a line B.1 to B.73 of Table B.

Table 53: Compounds of general formula (Ie) wherein $X_1$ and $X_2$ are bromine and n is 3, and the substituent R for each compound corresponds to a line B.1 to B.73 of Table B.

Table 54: Compounds of general formula (Id) wherein $X_1$ and $X_2$ are bromine and n is 4, and the substituent R for each compound corresponds to a line B.1 to B.73 of Table B.

Table 55: Compounds of general formula (Ie) wherein $X_1$ and $X_2$ are bromine and n is 4, and the substituent R for each compound corresponds to a line B.1 to B.73 of Table B.

Table 56: Compounds of general formula (If) wherein $X_1$ and $X_2$ are bromine and n is 4, and the substituent R for each compound corresponds to a line B.1 to B.73 of Table B.

Formulation Examples (%=Percent by Weight)

| Example F1: Emulsifiable concentrates | a) | b) | c) |
|---|---|---|---|
| active ingredient | 25% | 40% | 50% |
| calcium dodecylbenzenesulfonate | 5% | 8% | 6% |
| castor oil polyethylene glycol ether (36 mol EO) | 5% | — | — |
| tributylphenol polyethylene glycol ether (30 mol EO) | — | 12% | 4% |
| cyclohexanone | — | 15% | 20% |
| xylene mixture | 65% | 25% | 20% |

Mixing finely ground active ingredient and additives gives an emulsifiable concentrate which yields emulsions of the desired concentration on dilution with water.

| Example F2: Solutions | a) | b) | c) | d) |
|---|---|---|---|---|
| active ingredient | 80% | 10% | 5% | 95% |
| ethylene glycol monomethyl ether | 20% | — | — | — |

-continued

| Example F2: Solutions | a) | b) | c) | d) |
|---|---|---|---|---|
| polyethylene glycol (MW 400) | — | 70% | — | — |
| N-methylpyrrolid-2-one | — | 20% | — | — |
| epoxidised coconut oil | — | — | 1% | 5% |
| benzine (boiling range: 160–190°) | — | — | 94% | — |

Mixing finely ground active ingredient and additives gives a solution suitable for use in the form of microdrops.

| Example F3: Granules | a) | b) | c) | d) |
|---|---|---|---|---|
| active ingredient | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in dichloromethane, the solution is sprayed onto the carrier mixture and the solvent is evaporated off in vacuo.

Biological Examples

Example B1

Action Against *Heliothis virescens* Caterpillars

Young soybean plants are sprayed with an aqueous emulsion spray mixture comprising 400 ppm of test compound. After the spray-coating has dried, the soybean plants are populated with 10 caterpillars of *Heliothis virescens* in the first stage and placed in a plastics container. Evaluation is made 6 days later. The percentage reduction in population and the percentage reduction in feeding damage (% activity) are determined by comparing the number of dead caterpillars and the feeding damage on the treated plants with that on the untreated plants.

The compounds of the Tables exhibit good activity against *Heliothis virescens* in this test. In particular, the compounds 1.3, 1.4, 1.6 and 1.10 are more than 80% effective.

Example B2

Action Against *Plutella xylostella* Caterpillars

Young cabbage plants are sprayed with an aqueous emulsion spray mixture comprising 400 ppm of test compound. After the spray-coating has dried, the cabbage plants are populated with 10 caterpillars of *Plutella xylostella* in the third stage and placed in a plastics container. Evaluation is made 3 days later. The percentage reduction in population and the percentage reduction in feeding damage (% activity) are determined by comparing the number of dead caterpillars and the feeding damage on the treated plants with that on the untreated plants.

The compounds of the Tables exhibit good activity against *Plutella xylostella*. In particular, the compounds 1.4 to 1.12 and 1.18 are more than 80% effective.

Example B3

Action Against *Spodoptera littoralis*

Young soybean plants are sprayed with an aqueous emulsion spray mixture comprising 400 ppm of test compound and, after the spray-coating has dried, the plants are populated with 10 caterpillars of *Spodoptera littoralis* in the first stage and then placed in a plastics container. 3 days later, the percentage reduction in population and the percentage reduction in feeding damage (% activity) are determined by comparing the number of dead caterpillars and the feeding damage on the treated plants with that on untreated plants.

The compounds of the Tables exhibit good activity in this test. In particular, the compounds 1.3 to 1.7, 1.9 to 1.12 and 1.18 are more than 80% effective.

What is claimed is:

1. A compound of formula

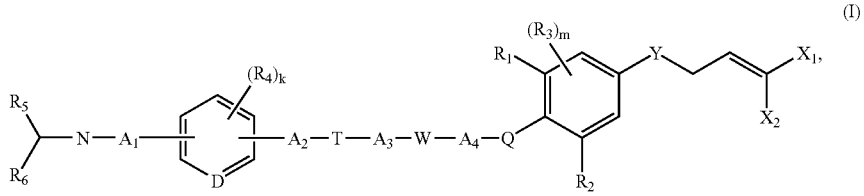

(I)

wherein $A_1$, $A_2$ and $A_3$ are each independently of the others a bond or a $C_1$–$C_6$alkylene bridge which is unsubstituted or substituted by from one to six identical or different substituents selected from $C_3$–$C_8$cycloalkyl, $C_3$–$C_8$cycloalkyl-$C_1$–$C_6$alkyl and $C_1$–$C_3$haloalkyl;

$A_4$ is a $C_1$–$C_6$alkylene bridge which is unsubstituted or substituted by from one to six identical or different substituents selected from $C_3$–$C_8$cycloalkyl, $C_3$–$C_8$cycloalkyl-$C_1$–$C_6$alkyl and $C_1$–$C_3$haloalkyl;

D is CH;

T is a bond, O, NH, $NR_7$, S, SO, $SO_2$, —C(=O)—O—, —O—C(=O)—, —C(=O)—$NR_8$— or —$NR_8$—C(=O)—;

W is O, $NR_7$, S, SO, $SO_2$, —C(=O)—O—, —O—C(=O)—, —C(=O)—$NR_8$— or —$NR_8$—C(=O)—;

Q is O, $NR_7$, S, SO or $SO_2$;

Y is O, $NR_7$, S, SO or $SO_2$;

$X_1$ and $X_2$ are each independently of the other fluorine, chlorine or bromine;

$R_1$, $R_2$ and $R_3$ are each independently of the others H, halogen, CN, nitro, $C_1$–$C_6$alkyl, $C_1$–$C_6$haloalkyl, $C_1$–$C_6$alkylcarbonyl, $C_2$–$C_6$alkenyl, $C_2$–$C_6$haloalkenyl, $C_2$–$C_6$alkynyl, $C_1$–$C_6$alkoxy, $C_1$–$C_6$haloalkoxy, $C_2$–$C_6$alkenyloxy, $C_2$–$C_6$haloalkenyloxy, $C_2$–$C_6$alkynyloxy, $C_1$–$C_6$alkoxycarbonyl or $C_2$–$C_6$haloalkenyloxy; the substituents $R_3$ being independent of one another when m is 2;

$R_4$ is H, halogen, CN, nitro, $C_1$–$C_6$alkyl, $C_1$–$C_6$haloalkyl, $C_1$–$C_6$alkylcarbonyl, $C_2$–$C_6$alkenyl, $C_2$–$C_6$haloalkenyl, $C_2$–$C_6$alkynyl, $C_1$–$C_6$alkoxy, $C_1$–$C_6$haloalkoxy, $C_2$–$C_6$alkenyloxy, $C_2$–$C_6$haloalkenyloxy, $C_2$–$C_6$alkynyloxy, $C_1$–$C_6$alkoxycarbonyl or $C_2$–$C_6$haloalkenyloxy; the substituents $R_4$ being independent of one another when k is greater than 1;

$R_5$ is H, CN, OH, $C_1$–$C_6$alkyl, $C_3$–$C_8$cycloalkyl, $C_3$–$C_8$cycloalkyl-$C_1$–$C_6$alkyl, $C_1$–$C_6$haloalkyl, $C_1$–$C_6$alkoxy, $C_1$–$C_6$haloalkoxy, $C_2$–$C_6$alkenyloxy, $C_2$–$C_6$haloalkenyloxy, $C_2$–$C_6$alkynyloxy, —C(=O)$R_9$, —C(=S)$R_9$, phenyl, benzyl; or phenyl or benzyl each of which is substituted in the aromatic ring by from one to five identical or different substituents selected from the group consisting of halogen, $C_1$–$C_6$alkyl, halo-$C_1$–$C_6$alkyl, $C_1$–$C_6$alkoxy, halo-$C_1$–$C_6$alkoxy, hydroxy, cyano and nitro;

$R_6$ is H, CN, $C_1$–$C_6$alkyl, $C_3$–$C_8$cycloalkyl, $C_3$–$C_8$cycloalkyl-$C_1$–$C_6$alkyl, $C_1$–$C_6$haloalkyl, —C(=O)$R_9$, —C(=S)$R_9$, phenyl, benzyl; or phenyl or benzyl each of which is substituted in the aromatic ring by from one to five identical or different substituents selected from the group consisting of halogen, $C_1$–$C_6$alkyl, halo-$C_1$–$C_6$alkyl, $C_1$–$C_6$alkoxy, halo-$C_1$–$C_6$alkoxy, hydroxy, cyano and nitro; or $R_5$ and $R_6$ together form a four- to eight-membered alkylene or a four- to eight-membered alkenylene bridge wherein a $CH_2$ group may have been replaced by O, S or $NR_{10}$, and the alkylene or alkenylene bridge is unsubstituted or substituted by from one to four identical or different substituents selected from $C_1$–$C_6$alkyl, $C_3$–$C_8$cycloalkyl, $C_3$–$C_8$cycloalkyl-$C_1$–$C_6$alkyl, $C_1$–$C_3$haloalkyl, CN and —C(=O)$C_1$–$C_6$alkyl; or $R_6$ is —C(=O)$R_9$ or —C(=S)$R_9$, and $R_5$ and $R_9$ together form a two- to eight-membered alkylene or a two- to eight-membered alkenylene bridge wherein a $CH_2$ group may have been replaced by O, S or $NR_{10}$, and wherein the alkylene or alkenylene bridge is unsubstituted or substituted by from one to four identical or different substituents selected from $C_1$–$C_6$alkyl, $C_3$–$C_8$cycloalkyl, $C_3$–$C_8$cycloalkyl-$C_1$–$C_6$alkyl, $C_1$–$C_3$haloalkyl, CN and —C(=O)$C_1$–$C_6$alkyl; or $R_5$ and $R_6$ are each independently of the other —C(=O)$R_9$ or —C(=S)$R_9$, and the two $R_9$ together form a two- to eight-membered, straight-chain or branched alkylene or a two- to eight-membered alkenylene bridge wherein a $CH_2$ group may have been replaced by O, S or $NR_{10}$; and wherein the alkylene or alkenylene bridge is unsubstituted or substituted by from one to four identical or different substituents selected from $C_1$–$C_6$alkyl, $C_3$–$C_8$cycloalkyl, $C_3$–$C_8$cycloalkyl-$C_1$–$C_6$alkyl, $C_1$–$C_3$haloalkyl, CN and —C(=O)$C_1$–$C_6$alkyl;

$R_7$ is H, $C_1$–$C_6$alkyl, $C_1$–$C_3$haloalkyl, $C_1$–$C_3$haloalkylcarbonyl, $C_1$–$C_6$alkoxyalkyl, $C_1$–$C_6$alkylcarbonyl or $C_3$–$C_8$cycloalkyl;

$R_8$ is H, $C_1$–$C_6$alkyl, $C_1$–$C_3$haloalkyl, $C_1$–$C_3$haloalkylcarbonyl, $C_1$–$C_6$alkoxyalkyl, —C(=O)$C_1$–$C_6$alkyl or $C_3$–$C_8$cycloalkyl;

R$_9$ is C$_1$–C$_6$alkyl, C$_1$–C$_6$haloalkyl, C$_2$–C$_6$alkenyl, C$_2$–C$_6$haloalkenyl, C$_2$–C$_6$alkynyl, C$_1$–C$_6$alkoxy, C$_1$–C$_6$haloalkoxy, C$_2$–C$_6$alkenyloxy, C$_2$–C$_6$haloalkenyloxy, C$_2$–C$_6$alkynyloxy, C$_3$–C$_6$cycloalkyl, phenyl, benzyl; or phenyl or benzyl each of which is unsubstituted or substituted by from one to three identical or different substituents selected from halogen, CN, nitro, C$_1$–C$_6$alkyl, C$_1$–C$_6$haloalkyl, C$_1$–C$_6$alkylcarbonyl, C$_2$–C$_6$alkenyl, C$_2$–C$_6$haloalkenyl, C$_2$–C$_6$alkynyl, C$_1$–C$_6$alkoxy, C$_1$–C$_6$haloalkoxy, C$_1$–C$_6$alkoxycarbonyl, C$_1$–C$_3$haloalkoxycarbonyl and C$_2$–C$_6$haloalkenyloxy;

R$_{10}$ is H, C$_1$–C$_6$alkyl, C$_1$–C$_3$haloalkyl, C$_1$–C$_3$haloalkylcarbonyl, C$_1$–C$_6$alkoxyalkyl, C$_1$–C$_6$alkylcarbonyl or C$_3$–C$_8$cycloalkyl;

k, or, when D is CH, is 1, 2, 3 or 4; and m is 1 or 2;

and, where applicable, a possible E/Z isomer, E/Z isomeric mixture and/or tautomer thereof, in each case in free form or in salt form.

2. A compound according to claim 1 of formula (I) in free form.

3. A compound according to claim 1 of formula (I) wherein X$_1$ and X$_2$ are chlorine or bromine.

4. A pesticidal composition which comprises as active ingredient at least one compound according to claim 1 of formula (I), in free form or in agrochemically acceptable salt form, and at least one adjuvant.

5. A process for the preparation of a composition as described in claim 1 which comprises mixing the active ingredient, of formula 1, according to claim 1, with at least one adjuvant.

6. A method of controlling pests which comprises applying a pesticidal composition as described in claim 1 to the pests or to the locus.

7. A compound according to claim 3 in free form.

8. A compound according to claim 1, wherein:

A$_2$ is a bond;

W is —C(=O)—NR$_8$;

A$_4$ is a C$_1$–C$_6$alkylene bridge which is unsubstituted or substituted by from one to six identical or different substituents selected from C$_3$–C$_8$cycloalkyl, C$_3$–C$_8$cycloalkyl-C$_1$–C$_6$alkyl and C$_1$–C$_3$haloalkyl;

Q is O; and

Y is O.

9. A pesticidal composition which comprises as active ingredient at least one compound according to claim 8, in free form or in agrochemically acceptable salt form, and at least one adjuvant.

10. A method of controlling pests which comprises applying a pesticidal composition as described in claim 9 to the pests or to the locus.

* * * * *